United States Patent
Baird et al.

(10) Patent No.: US 10,724,104 B2
(45) Date of Patent: Jul. 28, 2020

(54) PROGNOSTIC MEAN TELOMERE LENGTH

(71) Applicant: University College Cardiff Consultants Limited, Cardiff (GB)

(72) Inventors: Duncan Baird, Penarth (GB); Chris Pepper, Penarth (GB); Christopher Fegan, Penarth (GB)

(73) Assignee: UNIVERSITY COLLEGE CARDIFF CONSULTANTS LIMITED, Cardiff, Wales (GB)

(*) Notice: Subject to any disclaimer, the term of this patent is extended or adjusted under 35 U.S.C. 154(b) by 0 days.

(21) Appl. No.: 16/364,822

(22) Filed: Mar. 26, 2019

(65) Prior Publication Data

US 2019/0276898 A1    Sep. 12, 2019

Related U.S. Application Data

(63) Continuation of application No. 15/419,414, filed on Jan. 30, 2017, now Pat. No. 10,378,065, which is a continuation-in-part of application No. 14/238,763, filed as application No. PCT/GB2012/051936 on Aug. 9, 2012, now abandoned.

(30) Foreign Application Priority Data

Aug. 15, 2011 (GB) .................... 1113968.0

(51) Int. Cl.
  *C12Q 1/6886* (2018.01)
  *C12Q 1/6883* (2018.01)
(52) U.S. Cl.
  CPC ......... *C12Q 1/6886* (2013.01); *C12Q 1/6883* (2013.01); *C12Q 2600/106* (2013.01); *C12Q 2600/118* (2013.01); *C12Q 2600/156* (2013.01)
(58) Field of Classification Search
  None
  See application file for complete search history.

(56) References Cited

U.S. PATENT DOCUMENTS

| RE28,657 E | 12/1975 | Barger et al. | |
| 10,378,065 B2* | 8/2019 | Baird | C12Q 21/6883 |
| 2014/0024034 A1* | 1/2014 | Tanaka | C12Q 21/6883 435/6.12 |

FOREIGN PATENT DOCUMENTS

| WO | WO 2003/000927 | * | 1/2003 |
| WO | WO 2016/059398 | * | 4/2016 |

OTHER PUBLICATIONS

Tanaka et al PNAS. Aug. 28, 2012. 109(35): 14098-14103 and Supporting Information, p. 1-2 (Year: 2012).*
Lin et al. British J Haematology. 2014. 167: 214-223 and Supplementary Material p. 1-8 (Year: 2014).*
NCBI Database GenBank Accession No. AF027390.1, Apr. 2, 1998, available via URL: ncbi.nlm.nih.gov/nuccore/3004858?sat=13 &satkey=9638250> (Year: 1998).*
Lin et al.; "Telomere dysfunction and fusion during the progression of chronic lymphocytic leukemia: evidence for a telomere crisis"; Blood, vol. 116, No. 11, Sep. 16, 2010, pp. 1899-907.
International Search report and Written Opinion for International application No. PCT/GB2012/051936 dated Nov. 19, 2012.
Search Report for British application No. GB1113968.0 dated Dec. 15, 2011.
Capper, R. et al.; "The nature of telomere fusion and a definition of the critical telomere length in human cells"; Genes & Development; vol. 21, 2007, pp. 2495-250.
Letsolo, B. T. et al.; "Fusion of short telomeres in human cells is characterized by extensice deletion and microhomology, and can result in complex rearracngements", Nucleic Acids Research, vol. 38, No. 6; Dec. 21, 2009, pp. 1841-1852.
Baird, D. M. et al.; "Extensive allelic variation and ultrashort telomeres in senescent human cells"; Nature Genetics, vol. 33, 2003, pp. 203-207.
Britt-Compton, B. et al.; "Structural stability and chromosome-specific telomere length is governed by cis-acting determinants in humans", Human Molecular Genetics, vol. 15, No. 5, 2006, pp. 725-733.
Sellmann, et al., "Telomeres and prognosis in patients with chronic lymphocytic leukaemia," Int. J. Hematol. (2011) 93:74-82.
Grabowski, et al., "Telomere length as a prognostic parameter in chronic lymphocytic leukemia with special reference to VH gene mutation status," Blood, Jun. 15, 2005, vol. 105, No. 12.

* cited by examiner

*Primary Examiner* — Carla J Myers
(74) *Attorney, Agent, or Firm* — King & Schickli, PLLC

(57) ABSTRACT

The disclosure concerns a prognostic method for determining at least one, or a combination, of the following: time to first treatment, response to treatment or overall survival for a patient presenting with a disease including or characterised by telomere shortening, including an assessment of the longest mean telomere length at which telomere end-end fusion events can be detected and then a determination of the mean telomere length in the fusogenic range (i.e. the range below that mean telomere length at which telomere end-end fusion events can be detected) and the subsequent use of the mean telomere length in the fusogenic range as a prognostic indicator.

8 Claims, 24 Drawing Sheets
Specification includes a Sequence Listing.

□ no telomere fusion
▨ telomere fusion
▩ unanalyzed for fusion

□ no telomere fusion
▨ telomere fusion
▪ unanalyzed for fusion

PROGNOSTIC MEAN TELOMERE LENGTH

This application is a continuation application claiming priority to U.S. patent application Ser. No. 15/419,414 filed on Jan. 30, 2017, which in turn claims priority as a continuation-in-part of U.S. patent application Ser. No. 14/238,763 filed on Apr. 23, 2014, which in turn claims priority from international patent application no. PCT/GB2012/051936 filed on Aug. 9, 2012, which in turn claims priority from British Patent Application Ser. No. 1113968.0 filed on Aug. 15, 2011, the disclosures of which are incorporated herein by reference in their entirety.

REFERENCE TO SEQUENCE LISTING SUBMITTED ELECTRONICALLY

A sequence listing electronically submitted with the present application as an ASCII text file named 1776-020_CIP_Cont_SequenceListing_ST25.txt, created on 3-21-2019 and having a size of 8000 bytes, is incorporated herein by reference in its entirety.

TECHNICAL FIELD

The disclosure relates to a novel prognostic method for determining at least one, or a combination, of the following: time to first treatment, response to treatment or overall survival for a patient presenting with a disease including or characterised by telomere shortening, comprising an assessment of the longest mean telomere length at which telomere end-end fusion events can be detected and then a determination of the mean telomere length in the fusogenic range (i.e. the range below said mean telomere length at which telomere end-end fusion events can be detected) and the subsequent use of the mean telomere length in the fusogenic range as a prognostic indicator. The disclosure also relates to the use of said method in a treatment regimen.

BACKGROUND

Chronic lymphocytic leukaemia (CLL) is the most common adult leukaemia, characterised by the accumulation of immuno-incompetent, monoclonal $CD5^+$ B-lymphocytes. CLL has a very heterogeneous clinical course with survival ranging from a few months to many decades. Treatment strategies vary with staging and disease progression and include chemotherapy, radiotherapy, monoclonal antibody therapy or bone marrow transplantation, with early stage patients often receiving no treatment. Early clinical intervention is required for patients with an aggressive form of the disease, whereas patients with more benign forms simply need monitoring for disease progression at which point appropriate treatment may be administered. In this latter respect, it has been shown that early stage CLL intervention does not improve survival rates. It is therefore inappropriate to expose someone presenting with a disease that is unlikely to be life-threatening for up to 30 years with highly dangerous chemotherapeutic drugs. A reliable method for distinguishing the various forms of the disease is therefore desirable. Although the Binet and Rai staging systems are reliable predictors of clinical outcome between the staging groups, they fail to identify good and poor prognostic subsets within each stage. Since most patients present with early stage disease at diagnosis, a number of laboratory tests have been developed to try and predict the clinical course of these patients, most notably, immunoglobulin variable heavy chain somatic mutation status, CD38 expression, T-cell tyrosine kinase (ZAP-70) expression and cytogenetic abnormalities. Unmutated IGHV genes, high CD38 expression, high ZAP-70 expression and the presence of 17p and 11q deletions are all associated with a poor prognosis. The exploitation of this sort of laboratory data to provide a prognostic assay is described in US 2008/0026383. However, none of these individual markers can provide definitive prognostic information alone and when used in combination offer only a reasonable prognostic prediction.

Breast cancer is another very common tumour type in the western world. Breast tumours can be surgically removed but remnants of the tumour can remain resulting in the reoccurrence of the disease. Patients therefore have adjuvant treatments that have toxic side effects, and the suspicion is that many patients receive treatment that will not be beneficial to them. The usual approach is to tailor the aggressiveness of the chemotherapy to the risk of recurrence. As compared with standard chemotherapy, aggressive chemotherapy is associated with a greater benefit, but also with more acute and long-term toxic effects such as leukaemia and heart failure. As with CLL, there is thus a requirement for markers that allow prognostication following surgery for breast cancer. Gene expression arrays have been employed to identify specific gene expression signatures that are indicative of prognosis; these provide hazard ratios of up to 3.4 for overall survival in node negative breast cancer patients. Gene expression arrays are amongst the best markers of prognostication currently available for Breast cancer.

Myelodysplastic syndromes (MDS) are a heterogeneous collection of disorders of the bone marrow haematopoietic stem cells characterised by disruption to haematopoiesis ultimately leading to bone marrow failure. This condition was previously known as 'pre-leukaemia' because one third of patients progress to acute myeloid leukaemia (AML). There is therefore a clinical need to distinguish patients that progress to AML, and thus may require therapy from those that manifest a more benign form of the disease. Like CLL, MDS is characterised by large-scale unbalanced chromosomal rearrangements; these types of rearrangements are consistent with telomere dysfunction. Furthermore, there is evidence of telomere erosion in MDS and that mutation in the telomerase RNA components can confer MDS in children.

It follows from the above, that there is a range of diseases for which relatively early stage prognostication would be advantageous. Moreover, many of these diseases are characterised by genetic abnormalities and, specifically telomere shortening. These diseases include alzheimer's disease[1], brain infarction[1], heart disease[1], chronic HIV infection[1], chronic hepatitis[1], skin diseases[1], chronic inflammatory bowel disese[1] including ulcerative colitis, anaemia[1], atherosclerosis[1], Barrett's oesophagus and cancers[1] including precancerous conditions. The disclosure therefore has application to all of these diseases.

Telomeres are nucleoprotein structures composed of repetitive DNA sequences that cap the ends of linear eukaryotic chromosomes, protecting them from deterioration or fusion with adjacent chromosomes. During replication of DNA, the ends of chromosomes cannot be processed, and as a result during cell division the chromosome ends would be lost; telomeres however prevent this by themselves being consumed during each stage of cell division, essentially 'capping' the chromosome. Telomere ends are, however, maintained in certain cell types such as germ cells, stem cells and certain white blood cells, by the reverse transcriptase telomerase that catalyses the RNA templated addition of telomere repeats. Telomere length is a key determinant of telomeric function and it has been shown that short dysfunctional telomeres can drive genomic instability and tumourigenesis in mouse models. Furthermore, deregulation of telomerase has been shown to drive oncogenesis. Additionally, the loss of telomeres in somatic cells has been linked to replicative senescence preventing genomic instability and cancer. Conversely, it has also been shown that malignant cells can bypass this senescence and become immortalised by telomere extension by aberrant activation of telomerase.

SUMMARY

Consistent with the role of telomere biology in tumour progression, there is now a substantial body of evidence indicating that telomere length can provide prognostic information in many human malignancies including CLL[2-9]. However, there is a lack of resolution in the currently available technologies and this has hampered progress in translating telomeric assays into clinical practice. For example, a putative role of telomere dysfunction during the progression of breast cancer has been shown,[10] and low-resolution telomere length has been shown to provide limited prognostic information[11,12]. A key problem with these technologies is that they are based on hybridisation of DNA probes to telomere repeat units. Consequently, as telomeres get shorter there is less probe target, and thus short telomeres are not detectable[13,14]. This is important because it is the shortest telomeres that become dysfunctional and are subject to fusion, causing genomic instability that can drive the progression of human cancers[15-17]. Q-PCR-based methods have also been described for the estimation of telomere repeat content (WO 2004068110US), these allow for high throughput analysis. However the linearity of these methods for the detection of short telomeres (<4 kb) has not been established[18], this, coupled with the reported high CV values of up to 28%, renders the Q-PCR methods inappropriate for the detection of short telomeres and using this information as a prognostic tool for clinical decision making[19]. Hitherto, telomere analysis using existing low-resolution techniques is not a sufficiently informative prognostic marker.

To address this problem, we have previously developed single-molecule technologies that allow us to detect the presence of critically shortened telomeres[20,21] and to characterise telomere end-end fusions[16,17]. Single telomere length analysis (STELA) allows complete resolution of telomere lengths at specific chromosome ends, including telomeres in the length range in which telomere end-end fusions can occur[16,20]. It therefore permits detection of short telomeres that are potentially dysfunctional and capable of fusion. In part of this study the XpYp telomere was chosen for use in STELA because in contrast to 13q, 6q, 17p and 11q, there is no evidence to implicate the loss of this telomere in the pathology of CLL in particular. Furthermore our previous data indicate that the XpYp telomere length is representative of the genome-wide telomere length[20,22], and that telomerase-expressing cells can homogenise telomere lengths at different chromosome ends[15,23]. Using these tools, we have demonstrated a link between short telomeres, telomere end-end fusion events and genomic instability in diseases such as, but not limited to, CLL breast cancer and MDS.

In our investigations, we have used telomere length and fusion analysis to provide a definition of telomere dysfunction and then we have used this as a prognostic tool. Specifically, we have identified the longest mean telomere length at which telomere end-end fusion events can be detected for a selected chromosome, examples are shown in Table 1. Using this upper limit for fusion event detection we have been able to show that the mean telomere length in the fusogenic range (i.e. ≤ the upper limit) provides a biological parameter that is highly prognostic for at least one of the following: time to first treatment, response to treatment or overall survival. Furthermore, this biological parameter can also be used to provide remarkable prognostic resolution in early stage disease patients in terms of time to first treatment, response to treatment or overall survival; indeed, patients in the longer telomere subset showed an overall survival rate of 96% at 10 years. The longest mean telomere length at which telomere end-end fusion events can be detected therefore represents an indication of the mean telomere length at which telomeres become dysfunctional and capable of fusion. Knowledge of the length of an individual's telomeres and so the likelihood of end-end fusion events enables one to predict where the individual is placed with respect to disease progression and so ensures the individual receives treatment commensurate with their requirements; no less and no more. Further, the test to assess the length of an individual's telomeres can be repeated periodically to monitor disease progression.

We have been able to show that by applying a telomere length threshold based on telomere dysfunction, we are surprisingly able to transform the prognostic power of telomere length analysis. Thus in contrast to previous reports using low-resolution telomere length analysis (i.e. those methods described above that measure telomere length at 4 kb and above), our data indicate that high-resolution telomere length analysis (i.e. using, e.g. the STELA method, or any other method which can measure the full range of telomere length from one TTAGGG repeat to over 25 kb of telomere length) coupled with a definition of telomere dysfunction or a knowledge of our biological parameter, is sufficient for accurate prognostication in various diseases characterised by telomere shortening, including cancers.

According to a first aspect of the disclosure there is provided a prognostic method for determining the progression of a disease including or characterized by telomere shortening comprising:

i) using high-resolution telomere length analysis to determine the longest mean telomere length at which telomere end-end fusion events can be detected in samples of tissue from a number of individuals presenting with the same disease, in order to identify a threshold figure that represents an indication of the mean telomere length at which telomeres become dysfunctional and capable of fusion wherein said analysis comprises undertaking a PCR reaction using anyone or more primers specific for chromosome XpYp selected from the group comprising or consisting of:

```
                            (SEQ ID NO: 11)
TTGTCTCAGGGTCCTAGTG;

(SEQ ID NO: 12)
GGTTATCAACCAGGTGCTCT;

(SEQ ID NO: 13)
GGTTATCGACCAGGTGCTCC;

(SEQ ID NO: 14)
TGTGTCTGGAATTGGTGGGTT;

(SEQ ID NO:15)
CCTAGTGTGTCTGGAATTGGTTC;
```

-continued

ACCAGGTTTTCCAGTGTGTT;  (SEQ ID NO: 1)

CAGGGACCGGGACAAATAGAC;  (SEQ ID NO: 16)

CCTGTAACGCTGTTAGGTAC;  (SEQ ID NO: 4)

ACCAGGGGCTGATGTAACG;  (SEQ ID NO: 24)

TCTCAGGGTCCTAGTGTG;  (SEQ ID NO: 25)

GTTGTCTCAGGGTCCTAG;  (SEQ ID NO: 26)

GGGGTTGTCTCAGGGTCC;  (SEQ ID NO: 27)

TTCTAGGGGTTGTCTCAG;  (SEQ ID NO: 28)

TCTTCTAGGGGTTGTCTC;  (SEQ ID NO: 29)

CTAATCTGCTCCCWCCCAC;  (SEQ ID NO: 30)

GTGAGAGCTCAAGGT GCAGAAG;  (SEQ ID NO: 31)

TGTCGGGGACTGGGTTAACAG;  (SEQ ID NO: 32)

GCTGAGAAAGACCTT TTCGTAC;  (SEQ ID NO: 33)
and

CAAAGTGTTTGCATCAGTACCTCAC  (SEQ ID NO: 34)

ii) determining the prognostic mean telomere length of samples of tissue from a number of individuals presenting with said disease, by taking those samples whose mean telomere length is less than said threshold and averaging the mean telomere length of those samples;
iii) determining the mean test telomere length of a sample taken from a patient suspected of having or presenting with said disease and, where said mean test telomere length is less than said prognostic mean telomere length, concluding time to first treatment is poor and/or response to treatment is poor and/or overall survival is poor; or
iv) determining the mean test telomere length of a sample taken from a patient suspected of having or presenting with said disease and, where said mean test telomere length is greater than said prognostic mean telomere length, concluding time to first treatment is good and/or response to treatment is good and/or overall survival is good.

Reference herein to a primer for use in any of the methods described herein and comprising the specified primer sequence is reference to a primer that is identical to the specified primer sequence or one that is, in ascending order of preference, 80%, 85%, 90%, 95%, 99% identical with said primer sequence.

Reference herein to a primer for use in any of the methods described herein and consisting of the specified primer sequence is reference to a primer that is identical to the specified primer sequence.

The disclosure therefore relates to identification of a specific methodology that permits critical telomeric parameters to be defined for a particular disease or, typically, malignancy. These parameters are the upper telomeric threshold for end-end fusion events, as in i) above, and a subsequent prognostic mean telomere length below the said threshold or in the fusogenic range, as in ii) above. Further, the method also involves an analysis of patient telomere distribution, as in iii) or iv) above, and by relating this to the determined threshold and said prognostic mean, the method predicts whether a patient will require treatment and it also predicts progression-free or overall survival of each patient at the time the method is undertaken.

In a further method, step i) additionally or alternatively comprises undertaking a PCR reaction using anyone or more primers specific for chromosome 7q selected from the group comprising or consisting of:

CCCACACAGTCATCTATTGTT;  (SEQ ID NO: 35)

GAGGTGCAGTAGTGGGATCTAACT;  (SEQ ID NO: 36)

GGGACAGCATATTCTGGTTT;  (SEQ ID NO: 37)

GCACAGCCTTTTGGGGTACCA;  (SEQ ID NO: 38)

AGTGGGAGATCCACACCGTAGCGTG;  (SEQ ID NO: 39)

CCaTGCAGTGCTAAGACAGCAATGAG;  (SEQ ID NO: 40)

GGGCACTGCCTCGCTTTGA;  (SEQ ID NO: 41)

GCAGTGCTAAGACAGCAATGAgAAc;  (SEQ ID NO: 42)

CAGTGCTAAGACAGCAATGAg;  (SEQ ID NO: 43)

ATCGGCATTCCCCACACTGCCa;  (SEQ ID NO: 44)

ATATAAGATCGGCATTCCC;  (SEQ ID NO: 45)
and

AGATCCACACCGTAGCGTg.  (SEQ ID NO: 46)

In yet another embodiment, step i) additionally or alternatively comprises undertaking a PCR reaction using anyone or more primers specific for chromosome 17p selected from the group comprising or consisting of:

GAATCCACGGATTGCTTTGTGTAC;  (SEQ ID NO: 17)

GGCTGAACTATAGCCTCTGC;  (SEQ ID NO: 2)
and

CCTGGCATGGTATTGACATG.  (SEQ ID NO: 5)

In yet another embodiment, step i) additionally or alternatively comprises undertaking a PCR reaction using a primer specific for chromosome 16p and comprising or consisting of:

GTGAATAATCAAGGTCAGAGCA. (SEQ ID NO: 18)

In yet another embodiment, step i) additionally or alternatively comprises undertaking a PCR reaction using a primer specific for chromosome 18q and comprising or consisting of:

CCTGTGGGTCTAAAACCAGAAGG (SEQ ID NO: 19)

In yet another embodiment, step i) additionally or alternatively comprises undertaking a PCR reaction using a primer specific for chromosome 2p2 and comprising or consisting of:

GAGCTGCGTTTTGCTGAGCAC. (SEQ ID NO: 20)

In yet another embodiment, step i) additionally or alternatively comprises undertaking a PCR reaction using a primer specific for chromosome 11q and comprising or consisting of:

CAGACCTTGGAGGCACGGCCTTCG. (SEQ ID NO: 21)

In yet another embodiment, step i) additionally or alternatively comprises undertaking a PCR reaction using a primer specific for chromosome 12q and comprising or consisting of:

GGGAGATCCACACCGTAGCA (SEQ ID NO: 22)
or
ACAGCCTTTTGGGGTACCGC. (SEQ ID NO: 23)

In yet another embodiment, said method comprises undertaking a number of tests using any selected number of primers to assay for more than one chromosome whereby a first test and then at least one further test is undertaken, sequentially or simultaneously, such that analysis of the telomere length of at least two chromosomes is undertaken. Ideally, a plurality of the following chromosomes, including any combination thereof, 7q, XpYp, 17p, 16, 18, 11q, and 12q chromosome are assayed such that analysis of the telomere length of at least two chromosomes is undertaken.

In an embodiment of the method said fusion event in part i) above is verified as being such by direct DNA sequence analysis before the data relating to same is included in the method.

Additionally or alternatively, in a further embodiment of the method, said prognostic mean telomere length of a sample of tissue from a number of individuals presenting with said disease is determined by taking those samples that exhibit telomere fusion and averaging the mean telomere length of those samples. This method therefore includes samples whose mean telomere length is less than said threshold and also samples whose mean telomere length is greater than said threshold but, regardless of this fact, only samples exhibiting fusion are used to generate an average telomere length. As those skilled in the art will appreciate, the fact that the method can be worked using this additional or alternative set of samples indicates that any telomere length below said threshold is prognostic; the mean thereof particularly so.

In a further embodiment of the method said disease including or characterised by telomere shortening comprises a disease where telomeres are shortened, as herein described, particularly where telomerase has reduced activity (statistically significant at the $P<0.05$ level) having regard to the average activity in immortalsied cell lines, and most preferably comprises one or more of the following diseases: ageing, alzheimer's disease; brain infarction; heart disease; chronic HIV infection; chronic hepatitis; skin diseases; chronic inflammatory bowel disease; ulcerative colitis; anaemia; atherosclerosis; Barrett's oesophagus; and cancer, including pre-cancerous conditions.

Said cancer may be either a haematological malignancy or a solid tumour.

Said cancer may be CLL, MDS or breast cancer.

The telomere length at which telomere end-end fusion events can be detected is, ideally but not necessarily, determined for a selected single chromosome. Examples of chromosomes on which this analysis has been undertaken are shown in Table 1 along with the value of the upper limit for end-end fusion detection for each chromosome. Using five examples we have shown that the upper limit for detecting end-end fusion events in different chromosomes is very similar i.e. between 3.81 and 5.01 kb. The mean is 4.52 kb with a standard deviation of only 0.46 kb. Similarly, we have also shown that the mean telomere length in the fusogenic range for these five chromosomes is also very similar i.e. between 2.26 and 3.01 kb. The mean is 2.69 kb with a standard deviation of only 0.30 kb.

In an alternative method, said telomere length at which telomere end-end fusion events can be detected is determined for a number of different chromosomes. Indeed, any chromosome could be used that can be subjected to high-resolution telomere length analysis. In this instance, the average upper limit for detecting end-end fusion events in the different chromosomes is used in part i) above; and the average mean telomere length in the fusogenic range for these different chromosomes in part ii) above is also used.

In an embodiment of the method, in the case where said disease is CLL, time to first treatment is poor means an individual has a median time to treatment of less than 2 years (i.e. 1.84 years) with a hazard ratio of 23.2 indicating that they are 23.2 times more likely to require treatment in unit time than an individual with telomere length above the threshold. Response to treatment is poor means a median time from first treatment to death of less than 5 years (i.e. 4.1 years) with a hazard ratio of 6.4 and overall survival is poor means a median survival time from diagnosis of less than 8 years (i.e. 7.49 years) with a hazard ratio of 71.3.

In an embodiment of the method, in the case where said disease is CLL, time to first treatment is good means an individual will not need treatment and can be monitored conventionally; and response to treatment is good means that the mean time to treatment will not be reached within 10 years; and overall survival is good means that the median survival is greater than 10 years with 96% of the cohort surviving to this censor point and can be monitored conventionally.

In an embodiment of the method, in the case where said disease is MDS, overall survival is poor means a median survival time from diagnosis of less than 1.5 years (i.e. 1.15 years) with a hazard ratio of 9.5.

In an embodiment of the method, in the case where said disease is MDS, overall survival is good means that the median survival is 4.9 years and can be monitored conventionally.

In an embodiment of the method, in the case where said disease is breast cancer, overall survival is poor means a median survival time of less than 1 year (i.e. 0.95 years) with a hazard ratio of 87080.

In an embodiment of the method, in the case where said disease is breast cancer, overall survival is good means that the median survival is greater than 6 years and can be monitored conventionally.

According to a second aspect there is provided a prognostic method for determining the progression of a disease including or characterized by telomere shortening comprising:

i) using high-resolution telomere length analysis to determine the prognostic mean telomere length of samples of tissue from a number of individuals presenting with said disease, whose mean telomere length is less than a 4.52 kb telomere length threshold at which telomere end-end fusion events can be detected in said cancerous disease, by taking those samples whose mean telomere length is less than said threshold and averaging the mean telomere length of those samples wherein said analysis comprises undertaking a PCR reaction using anyone or more primers specific for chromosome XpYp and selected from the group comprising or consisting of:

```
                                (SEQ ID NO: 11)
TTGTCTCAGGGTCCTAGTG;

(SEQ ID NO: 12)
GGTTATCAACCAGGTGCTCT;

(SEQ ID NO: 13)
GGTTATCGACCAGGTGCTCC;

(SEQ ID NO: 14)
TGTGTCTGGAATTGGTGGGTT;

(SEQ ID NO:15)
CCTAGTGTGTCTGGAATTGGTTC;

(SEQ ID NO: 1)
ACCAGGTTTTCCAGTGTGTT;

(SEQ ID NO: 16)
CAGGGACCGGGACAAATAGAC;

(SEQ ID NO: 4)
CCTGTAACGCTGTTAGGTAC;

(SEQ ID NO: 24)
ACCAGGGGCTGATGTAACG;

(SEQ ID NO: 25)
TCTCAGGGTCCTAGTGTG;

(SEQ ID NO: 26)
GTTGTCTCAGGGTCCTAG;

(SEQ ID NO: 27)
GGGGTTGTCTCAGGGTCC;

(SEQ ID NO: 28)
TTCTAGGGGTTGTCTCAG;

(SEQ ID NO: 29)
TCTTCTAGGGGTTGTCTC;

(SEQ ID NO: 30)
CTAATCTGCTCCCWCCCAC;
```

```
                                (SEQ ID NO: 31)
GTGAGAGCTCAAGGT GCAGAAG;

(SEQ ID NO: 32)
TGTCGGGGACTGGGTTAACAG;

(SEQ ID NO: 33)
GCTGAGAAAGACCTT TTCGTAC;
and (SEQ ID NO: 34)
CAAAGTGTTTGCATCAGTACCTCAC.
``` ii) determining the mean test telomere length of a sample taken from a patient suspected of having or presenting with said disease and, where said mean test telomere length is less than said prognostic mean telomere length, concluding the time to first treatment is poor and/or the response to treatment is poor and/or overall survival is poor; or iii) determining the mean test telomere length of a sample taken from a patient suspected of having or presenting with said disease and, where said mean test telomere length is greater than said prognostic mean telomere length, concluding time to first treatment is good and/or response to treatment is good and/or overall survival is good.

In this embodiment, preferably, said prognostic mean telomere length is determined using a 4.06 kb threshold (i.e. 4.52-0.46 kb) or a 4.98 kb threshold (i.e. 4.52+0.46 kb) at which telomere end-end fusion events can be detected.

In a further method of the second aspect, step i) additionally or alternatively comprises undertaking a PCR reaction using anyone or more primers specific for chromosome 7q and selected from the group comprising or consisting of:

```
                                (SEQ ID NO: 35)
CCCACACAGTCATCTATTGTT;

(SEQ ID NO: 36)
GAGGTGCAGTAGTGGGGATCTAACT;

(SEQ ID NO: 37)
GGGACAGCATATTCTGGTTT;

(SEQ ID NO: 38)
GCACAGCCTTTTGGGGTACCA;

(SEQ ID NO: 39)
AGTGGGAGATCCACACCGTAGCGTG;

(SEQ ID NO: 40)
CCaTGCAGTGCTAAGACAGCAATGAG;

(SEQ ID NO: 41)
GGGCACTGCCTCGCTTTGA;

(SEQ ID NO: 42)
GCAGTGCTAAGACAGCAATGAgAAc;

(SEQ ID NO: 43)
CAGTGCTAAGACAGCAATGAg;

(SEQ ID NO: 44)
ATCGGCATTCCCCACACTGCCa;

(SEQ ID NO: 45)
ATATAAGATCGGCATTCCC;
and (SEQ ID NO: 46)
AGATCCACACCGTAGCGTg
```

In yet a further embodiment of the second aspect, step i) additionally or alternatively comprises undertaking a PCR reaction using anyone or more primers specific for chromosome 17p selected from the group comprising or consisting of:

```
                                         (SEQ ID NO: 17)
        GAATCCACGGATTGCTTTGTGTAC;

(SEQ ID NO: 2)
        GGCTGAACTATAGCCTCTGC;
        and
                                         (SEQ ID NO: 5)
        CCTGGCATGGTATTGACATG
```

In yet a further embodiment of the second aspect, step i) additionally or alternatively comprises undertaking a PCR reaction using a primer specific for chromosome 16p and comprising or consisting of:

```
                                         (SEQ ID NO: 18)
        GTGAATAATCAAGGTCAGAGCA.
```

In yet a further embodiment of the second aspect, step i) additionally or alternatively comprises undertaking a PCR reaction using a primer specific for chromosome 18q and comprising or consisting of:

```
                                         (SEQ ID NO: 19)
        CCTGTGGGTCTAAAACCAGAAGG.
```

In yet a further embodiment of the second aspect, step i) additionally or alternatively comprises undertaking a PCR reaction using a primer specific for chromosome 2p2 and comprising or consisting of:

```
                                         (SEQ ID NO: 20)
        GAGCTGCGTTTTGCTGAGCAC.
```

In yet a further embodiment of the second aspect, step i) additionally or alternatively comprises undertaking a PCR reaction using a primer specific for chromosome 11q and comprising or consisting of:

```
                                         (SEQ ID NO: 21)
        CAGACCTTGGAGGCACGGCCTTCG.
```

In yet a further embodiment of the second aspect, step i) additionally or alternatively comprises undertaking a PCR reaction using a primer specific for 12q and comprising or consisting of:

```
                                         (SEQ ID NO: 22)
        GGGAGATCCACACCGTAGCA
        or
                                         (SEQ ID NO: 23)
        ACAGCCTTTTGGGGTACCGC
```

In yet a further embodiment, said method comprises undertaking a number of tests using any selected number of primers to assay for more than one chromosome whereby a first test and then at least one further test is undertaken, sequentially or simultaneously, such that analysis of the telomere length of at least two chromosomes is undertaken. Ideally, a plurality of the following chromosomes, including any combination thereof, 7q, XpYp, 17p, 16, 18, 11q, and 12q chromosome are assayed such that analysis of the telomere length of at least two chromosomes is undertaken.

In another embodiment of the second aspect said disease is cancer and, typically, said cancer is CLL, breast cancer or MDS and, ideally, said prognostic mean telomere length value of 2.26 kb is used for CLL and breast cancer and said prognostic mean telomere length value of 2.5 kb is used for MDS.

Still more, in this second aspect said telomere length at which telomere end-end fusion events can be detected is determined for a number of chromosomes. Ideally, the chromosomes are XpYp, 17p, 2p, 16p and 18q, although any other combination of chromosomes may be used and their average upper threshold at which telomere end-end fusion events can be detected is used in the above method.

According to a third aspect there is provided a prognostic method for determining the progression of a disease including or characterized by telomere shortening comprising:

1. determining the mean test telomere length of a sample taken from a patient suspected of having or presenting with said disease and, where said mean test telomere length is less than a prognostic mean telomere length of 2.69 kb, concluding the time to first treatment is poor and/or the response to treatment is poor and/or overall survival is poor; or
2. determining the mean test telomere length of a sample taken from a patient suspected of having or presenting with said disease and, where said mean test telomere length is greater than a prognostic mean telomere length of 2.69 kb, concluding the time to first treatment is good and/or the response to treatment is good and/or overall survival is good; wherein said mean telomere length is analysed using a method comprising undertaking a PCR reaction using anyone or more primers specific for chromosome XpYp and selected from the group comprising or consisting of:

```
                                         (SEQ ID NO: 11)
        TTGTCTCAGGGTCCTAGTG;

(SEQ ID NO: 12)
        GGTTATCAACCAGGTGCTCT;

(SEQ ID NO: 13)
        GGTTATCGACCAGGTGCTCC;

(SEQ ID NO: 14)
        TGTGTCTGGAATTGGTGGGTT;

(SEQ ID NO: 15)
        CCTAGTGTGTCTGGAATTGGTTC;

(SEQ ID NO: 1)
        ACCAGGTTTTCCAGTGTGTT;

(SEQ ID NO: 16)
        CAGGGACCGGGACAAATAGAC;

(SEQ ID NO: 4)
        CCTGTAACGCTGTTAGGTAC;

(SEQ ID NO: 24)
        ACCAGGGGCTGATGTAACG;

(SEQ ID NO: 25)
        TCTCAGGGTCCTAGTGTG;

(SEQ ID NO: 26)
        GTTGTCTCAGGGTCCTAG;

(SEQ ID NO: 27)
        GGGGTTGTCTCAGGGTCC;
```

TTCTAGGGGTTGTCTCAG; (SEQ ID NO: 28)

TCTTCTAGGGGTTGTCTC; (SEQ ID NO: 29)

CTAATCTGCTCCCWCCCAC; (SEQ ID NO: 30)

GTGAGAGCTCAAGGTGCAGAAG; (SEQ ID NO: 31)

TGTCGGGGACTGGGTTAACAG; (SEQ ID NO: 32)

GCTGAGAAAGACCTTTTCGTAC
and (SEQ ID NO: 33)

CAAAGTGTTTGCATCAGTACCTCAC. (SEQ ID NO: 34)

In this third aspect, preferably, said prognostic mean telomere length is either 2.39 kb (i.e. 2.69-0.3 kb) or 2.99 kb (i.e. 2.69+0.3 kb).

In a further method of the third aspect, step i) additionally or alternatively comprises undertaking a PCR reaction using anyone or more primers specific for chromosome 7q and selected from the group comprising or consisting of:

CCCACACAGTCATCTATTGTT (SEQ ID NO: 35)

GAGGTGCAGTAGTGGGGATCTAACT (SEQ ID NO: 36)

GGGACAGCATATTCTGGTTT (SEQ ID NO: 37)

GCACAGCCTTTTGGGGTACCA (SEQ ID NO: 38)

AGTGGGAGATCCACACCGTAGCGTG (SEQ ID NO: 39)

CCaTGCAGTGCTAAGACAGCAATGAG (SEQ ID NO: 40)

GGGCACTGCCTCGCTTTGA (SEQ ID NO: 41)

GCAGTGCTAAGACAGCAATGAgAAc (SEQ ID NO: 42)

CAGTGCTAAGACAGCAATGAg (SEQ ID NO: 43)

ATCGGCATTCCCCACACTGCCa (SEQ ID NO: 44)

ATATAAGATCGGCATTCCC (SEQ ID NO: 45)

AGATCCACACCGTAGCGTg (SEQ ID NO: 46)

In yet a further embodiment of the third aspect, step i) additionally or alternatively comprises undertaking a PCR reaction using anyone or more primers specific for chromosome 17p selected from the group comprising or consisting of:

GAATCCACGGATTGCTTTGTGTAC; (SEQ ID NO: 17)

GGCTGAACTATAGCCTCTGC; (SEQ ID NO: 2)
and

CCTGGCATGGTATTGACATG. (SEQ ID NO: 5)

In yet a further embodiment of the third aspect, step i) additionally or alternatively comprises undertaking a PCR reaction using a primer specific for chromosome 16p and comprising or consisting of:

GTGAATAATCAAGGTCAGAGCA. (SEQ ID NO: 18)

In yet a further embodiment of the third aspect, step i) additionally or alternatively comprises undertaking a PCR reaction using a primer specific for chromosome 18q and comprising or consisting of:

CCTGTGGGTCTAAAACCAGAAGG (SEQ ID NO: 19)

In yet a further embodiment of the third aspect, step i) additionally or alternatively comprises undertaking a PCR reaction using a primer specific for chromosome 2p2 and comprising or consisting of:

GAGCTGCGTTTTGCTGAGCAC (SEQ ID NO: 20)

In yet a further embodiment of the third aspect, step i) additionally or alternatively comprises undertaking a PCR reaction using a primer specific for chromosome 11q and comprising or consisting of:

CAGACCTTGGAGGCACGGCCTTCG (SEQ ID NO: 21)

In yet a further embodiment of the third aspect, step i) additionally or alternatively comprises undertaking a PCR reaction using a primer specific for chromosome 16p and comprising or consisting of:

GGGAGATCCACACCGTAGCA; (SEQ ID NO: 22)
or

ACAGCCTTTTGGGGTACCGC (SEQ ID NO: 23)

In yet a further embodiment, said method comprises undertaking a number of tests using any selected number of primers to assay for more than one chromosome whereby a first test and then at least one further test is undertaken, sequentially or simultaneously, such that analysis of the telomere length of at least two chromosomes is undertaken. Ideally, a plurality of the following chromosomes, including any combination thereof, 7q, XpYp, 17p, 16, 18, 11q, and 12q chromosome are assayed such that analysis of the telomere length of at least two chromosomes is undertaken.

In another embodiment of the third aspect said disease is a haematological cancer, and typically said cancer is CLL or MDS and, more ideally still, said prognostic mean telomere length is 2.26 kb for the former and 2.5 kb for the latter.

In another embodiment of the third aspect said disease is breast cancer and, more ideally still, said prognostic mean telomere length is 2.26 kb.

Yet more, in this third aspect said prognostic mean telomere length is determined for a number of chromosomes. Ideally, the chromosomes are XpYp, 17p, 2p, 16p and 18q, although any other combination of chromosomes may be used and their average prognostic mean telomere length is used in the above method.

According to a further aspect there is provided one or more, including combinations thereof, of the primers described herein.

According to a yet further aspect there is provided a treatment regimen including or comprising said afore prognostic method according to any aspect or embodiment.

In the claims which follow and in the preceding description, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments.

All references, including any patent or patent application, cited in this specification are hereby incorporated by reference. No admission is made that any reference constitutes prior art. Further, no admission is made that any of the prior art constitutes part of the common general knowledge in the art.

Particular features of each aspect may be as described in connection with any of the other aspects.

Other features will become apparent from the following examples. Generally speaking, the disclosed methods extend to any novel one, or any novel combination, of the features disclosed in this specification (including the accompanying claims and drawings). Thus, features, integers, characteristics, compounds or chemical moieties described in conjunction with a particular aspect, embodiment or example are to be understood to be applicable to any other aspect, embodiment or example described herein, unless incompatible therewith.

Moreover, unless stated otherwise, any feature disclosed herein may be replaced by an alternative feature serving the same or a similar purpose.

The methods will now be described by way of example only with reference to the following tables and figures:

Table-1 shows the longest mean telomere length at which telomere end-end fusion events can be detected for a range of chromosomes, including the mean thereof and the prognostic mean telomere length for each one of said chromosomes, including the mean thereof.

Table-2 shows a comparison of prognostic factors in univariate analysis, in terms of time to first treatment and overall survival.

Table-3 shows the clinical characteristics of the 184 CLL patient cohort.

Table-4 shows the analysis of concordant datasets combining telomere length analysis with known prognostic markers.

DETAILED DESCRIPTION

Methods

CLL Patients

Figures 1A, 1B:
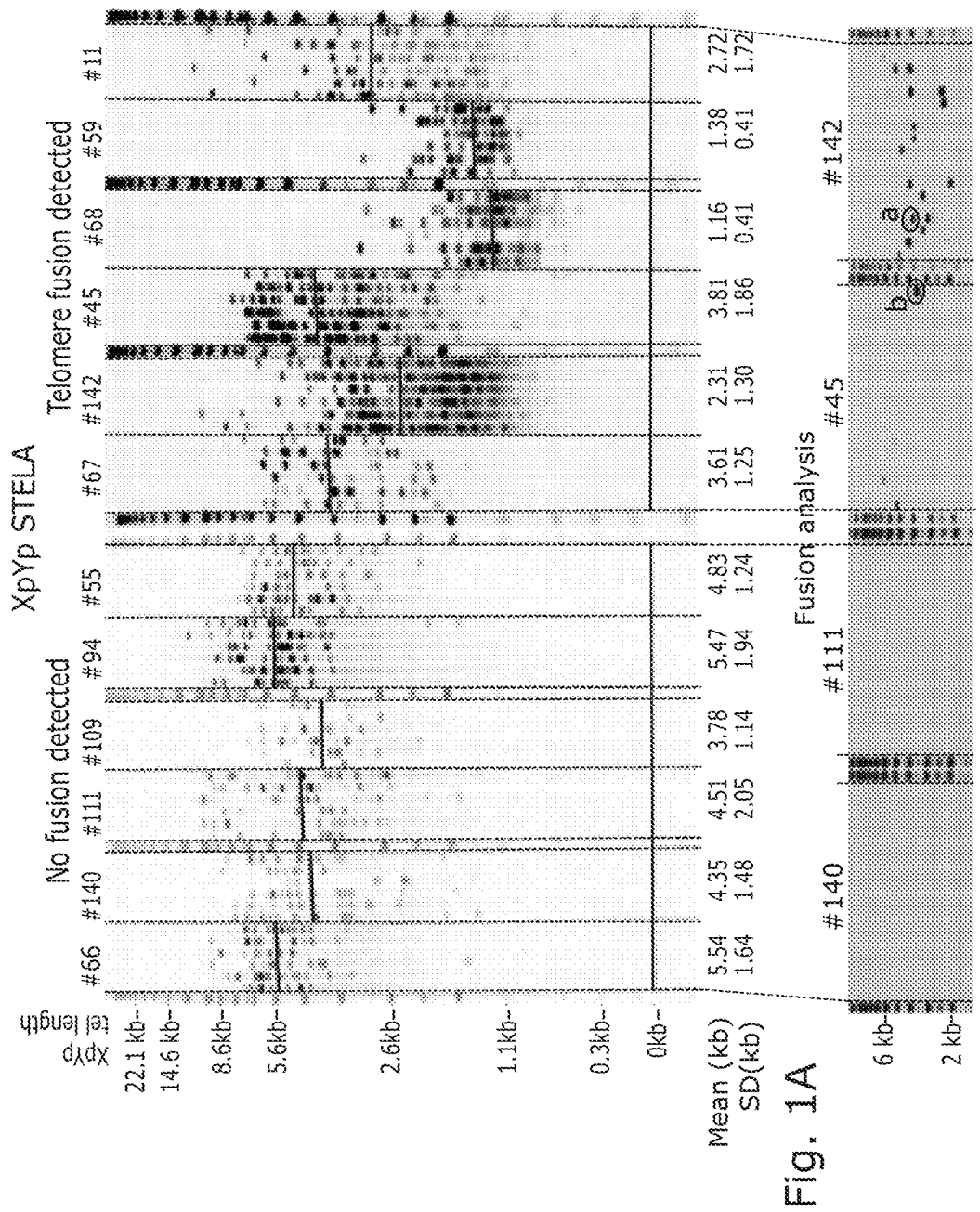
FIG. 1A defines the telomeric parameters for prognosis in CLL, showing an example of STELA at the XpYp telomere in 12 CLL patients in which fusion was, or was not detected. Mean and standard deviation are displayed below and the means highlighted in red on the gel image.
FIG. 1B shows examples of fusion analysis in 4 CLL patients.

Peripheral blood samples from 184 CLL consenting patients, in accordance with the Declaration of Helsinki and as approved by the South East Wales local research ethics committee (LREC#02/4806). CLL was defined by clinical criteria as well as cellular morphology, and also the co-expression of CD19 and CD5 in lymphocytes simultaneously displaying restriction of light-chain rearrangement. Comprehensive clinical information was available for all patients with a median follow-up of 5.8 years. All of the samples were collected at, or close to, the time of diagnosis from two centers, Cardiff and Birmingham, and staging was based on the Binet classification system[24]. The clinical characteristics of the CLL patient cohort are presented in Table-2.

Breast Cancer Patients

Genomic DNA, together with clinical follow up data, from a panel of 28 invasive breast ductal carcinomas was obtained from the Wales Cancer bank, under approval from the Wales MREC.

MDS Patients

Bone marrow samples were obtained from 63 patients diagnosed with myelodysplastic syndrome (MDS), as classified according to the French-American-British system. Of these, 40 patients were male and 23 were female, with a mean age at diagnosis of 67.5 years; the median follow-up for the cohort was 5.6 years. IPSS criteria were available for 55/63 patients with 15 high, 20 intermediate and 20 low.

Isolation of Peripheral Blood Mononuclear Cells from CLL Patients

Peripheral blood mononuclear cells (PBMCs) were isolated from EDTA venous blood of the 184 CLL patients by density centrifugation using Ficoll-Hypaque (Invitrogen). B-cells were subsequently positively isolated using CD19-labeled Dynabeads (Invitrogen)[25]. Cells were stored at −20° C. as dry pellets prior to DNA extraction.

DNA Extraction and PCR

DNA was extracted from human cells using standard proteinase K, RNase A, phenol/chloroform protocols[26]. For telomere length analysis at the XpYp, 17p, 2p, 16p, 7q and 18q telomeres, we used a modification of the single telomere length analysis (STELA) assay as previously described[16,20]. Briefly, genomic DNA was solubilized by dilution in 10 mM Tris-HCl (pH 7.5), quantified by using Hoechst 33258 fluorometry (BioRad, Hercules, USA), and diluted to 10 ng/μl in 10 mM Tris-HCl (pH 7.5). DNA (10 ng) was further diluted to 250 pg/μl in a volume of 40 μl, containing Telorette2 linker (1 μM) and Tris-HCl (1 mM; pH 7.5). Multiple PCR reactions (typically 6 reactions per sample) were carried out for each test DNA, in 10 μl volumes. The reaction mixture consisted of DNA (250 pg), telomere-adjacent and Teltail primers (0.5 μM), Tris-HCl (75 mM; pH8.8), $(NH_4)_2SO_4$ (25 mM), 0.01% Tween-20, $MgCl_2$ (1.5 mM), and 0.5 U of Taq (ABGene, Epsom, UK) and Pwo polymerase (Roche Molecular Biochemicals, Lewes, UK) in a 10:1 ratio. The reactions were cycled with an MJ PTC-225 thermocycler (MJ research, Watertown, USA). The DNA fragments were resolved by 0.5% TAE agarose gel electrophoresis, and detected by two separate Southern hybridizations, with random-primed α-33P labeled (Amersham Biosciences, Little Chalfont, UK) TTAGGG repeat probe and a telomere-adjacent probe, together with a probe to detect the 1 kb (Stratagene, La Jolla, USA) and 2.5 kb (BioRad) molecular weight marker. The hybridized fragments were detected by phosphorimaging with a Molecular Dynamics Storm 860 phosphorimager (Amersham Biosciences, Little Chalfont, UK). The molecular weights of the DNA fragments were calculated using the Phoretix 1D quantifier (Nonlinear Dynamics, Newcastle-upon-Tyne, UK).

Telomere fusion was detected using the previously described single molecule telomere fusion assays[16,17]. PCR reactions containing 100 ng of DNA were performed, each containing the XpYpM, 17p6 and 21q1 PCR primers. Fusion molecules were detected, and the frequencies quantified by Southern blotting and hybridization with the XpYp telomere-adjacent probes as described previously[5]. In order to determine the chromosomes participating in the fusion events for subsequent sequence characterization, further hybridisations were undertaken with the 17p and 21q telomere adjacent probes; the 21q probe yields additional non-specific products and thus was not used for quantification. Any fusion products were then re-amplified for direct sequence analysis using nested PCR primers (XpYpO, 17p7 and 21qseq1).

The oligonucleotides utilised were: XpYpM (5'-ACCAGGTTTTCCAGTGTGTT-3') (SEQ ID NO: 1), 17p6 (5'-GGCTGAACTATAGCCTCTGC-3') (SEQ ID NO: 2), 21q1 (5'-CTTGGTGTCGAGAGAGGTAG-3') (SEQ ID NO: 3) for fusion PCR; XpYpO (5'-CCTGTAACGCTGTTAGGTAC-3') (SEQ ID NO: 4), 17p7 (5'-CCTGGCATGGTATTGACATG-3') (SEQ ID NO: 5), 21qseq1 (5'-TGGTCTTATACACTGTGTTC-3') (SEQ ID NO: 6) for re-amplification of fusion products; 21qseq1 (5'-TGGTCTTATACACTGTGTTC-3') (SEQ ID NO: 6), 21qseq1rev (5'-AGCTAGCTATCTACTCTAACAGAGC-3') (SEQ ID NO: 7), XpYpO (5'-CCTGTAACGCTGTTAGGTAC-3') (SEQ ID NO: 4), XpYpB2 (5'-TCTGAAAGTGGACC(A/T)ATCAG-3') (SEQ ID NO: 8, SEQ ID NO: 9), 17p7 (5'-CCTGGCATGGTATTGACATG-3') (SEQ ID NO: 5), 17pseq3 (5'-AGAATCCTGTCCTCAACAAGT-3') (SEQ ID NO: 10) to generate hybridisation probes for fusion analysis.

Primers that can be used for STELA analysis (the ones that are typically used are italicised):

```
XpYpE2
                             (SEQ ID NO: 11)
TTGTCTCAGGGTCCTAGTG

XpYp-427A/415T
                             (SEQ ID NO: 12)
GGTTATCAACCAGGTGCTCT

XpYp-427G/415C
                             (SEQ ID NO: 13)
GGTTATCGACCAGGTGCTCC

XpYpins
                             (SEQ ID NO: 14)
TGTGTCTGGAATTGGTGGGTT

XpYpdel
                             (SEQ ID NO: 15)
CCTAGTGTGTCTGGAATTGGTTC

XpYpM
                             (SEQ ID NO: 1)
ACCAGGTTTTCCAGTGTGTT

XpYpC
                             (SEQ ID NO: 16)
CAGGGACCGGGACAAATAGAC

XpYpO
                             (SEQ ID NO: 4)
CCTGTAACGCTGTTAGGTAC

XpYpP
                             (SEQ ID NO: 24)
ACCAGGGGCTGATGTAACG

XpYpE3
                             (SEQ ID NO: 25)
TCTCAGGGTCCTAGTGTG

XpYpE4
                             (SEQ ID NO: 26)
GTTGTCTCAGGGTCCTAG

XpYpE5
                             (SEQ ID NO: 27)
GGGGTTGTCTCAGGGTCC

XpYpE6
                             (SEQ ID NO: 28)
TTCTAGGGGTTGTCTCAG

XpYpE7
                             (SEQ ID NO: 29)
TCTTCTAGGGGTTGTCTC

XpYpJ
                             (SEQ ID NO: 30)
CTAATCTGCTCCCWCCCAC

XpYpR
                             (SEQ ID NO: 31)
GTGAGAGCTCAAGGT GCAGAAG

XpYpS
                             (SEQ ID NO: 32)
TGTCGGGGACTGGGTTAACAG

XpYpT
                             (SEQ ID NO: 33)
GCTGAGAAAGACCTT TTCGTAC

XpYpU
                             (SEQ ID NO: 34)
CAAAGTGTTTGCATCAGTACCTCAC

17pseq1rev
                             (SEQ ID NO: 17)
GAATCCACGGATTGCTTTGTGTAC 17p6
                             (SEQ ID NO: 2)
GGCTGAACTATAGCCTCTGC 17p7
                             (SEQ ID NO: 5)
CCTGGCATGGTATTGACATG
```

-continued

16prev1
GTGAATAATCAAGGTCAGAGCA (SEQ ID NO: 18)

18qrev4
CCTGTGGGTCTAAAACCAGAAGG (SEQ ID NO: 19)

2p2
GAGCTGCGTTTTGCTGAGCAC (SEQ ID NO: 20)

11q13B
CAGACCTTGGAGGCACGGCCTTCG (SEQ ID NO: 21)

12q-197A
GGGAGATCCACACCGTAGCA (SEQ ID NO: 22)

12q-550C
ACAGCCTTTTGGGGTACCGC (SEQ ID NO: 23)

7q1532C
CCCACACAGTCATCTATTGTT (SEQ ID NO: 35)

7q1114T
GAGGTGCAGTAGTGGGGATCTAACT (SEQ ID NO: 36)

7q842T
GGGACAGCATATTCTGGTTT (SEQ ID NO: 37)

7q550A
GCACAGCCTTTTGGGGTACCA (SEQ ID NO: 38)

7q194G
AGTGGGAGATCCACACCGTAGCGTG (SEQ ID NO: 39)

7q28G
CCaTGCAGTGCTAAGACAGCAATGAG (SEQ ID NO: 40)

7qK1
GGGCACTGCCTCGCTTTGA (SEQ ID NO: 41)

7qF1
GCAGTGCTAAGACAGCAATGAgAAc (SEQ ID NO: 42)

7qG1
CAGTGCTAAGACAGCAATGAg (SEQ ID NO: 43)

7qH1
ATCGGCATTCCCCACACTGCCa (SEQ ID NO: 44)

7qI
ATATAAGATCGGCATTCCC (SEQ ID NO: 45)

7qJ
AGATCCACACCGTAGCGTg (SEQ ID NO: 46)

Statistical Methods

Statistical analysis was carried out using Prism 3.0 (Graphpad) and SAS version 9.1.3 software (SAS Institute).

The relationship between telomere length, known prognostic factors, time to first treatment (TTFT) and overall survival (OS) were explored through Wilcoxon rank sum tests for the categorical variables Binet stage, CD38, ZAP-70, IGHV gene mutation status, β2-microglobulin and FISH cytogenetics. Unstratified univariate comparisons of survival between the prognostic subsets were conducted with the log-rank test, with survival data displayed using Kaplan-Meier curves. Multivariate analysis, which adjusted for other prognostic features, was performed using forward selection to define significant co-variables with Cox regression. A P-value <0.05 was considered significant.

Results

Telomere Length and Fusion Analysis

Figure 1C:
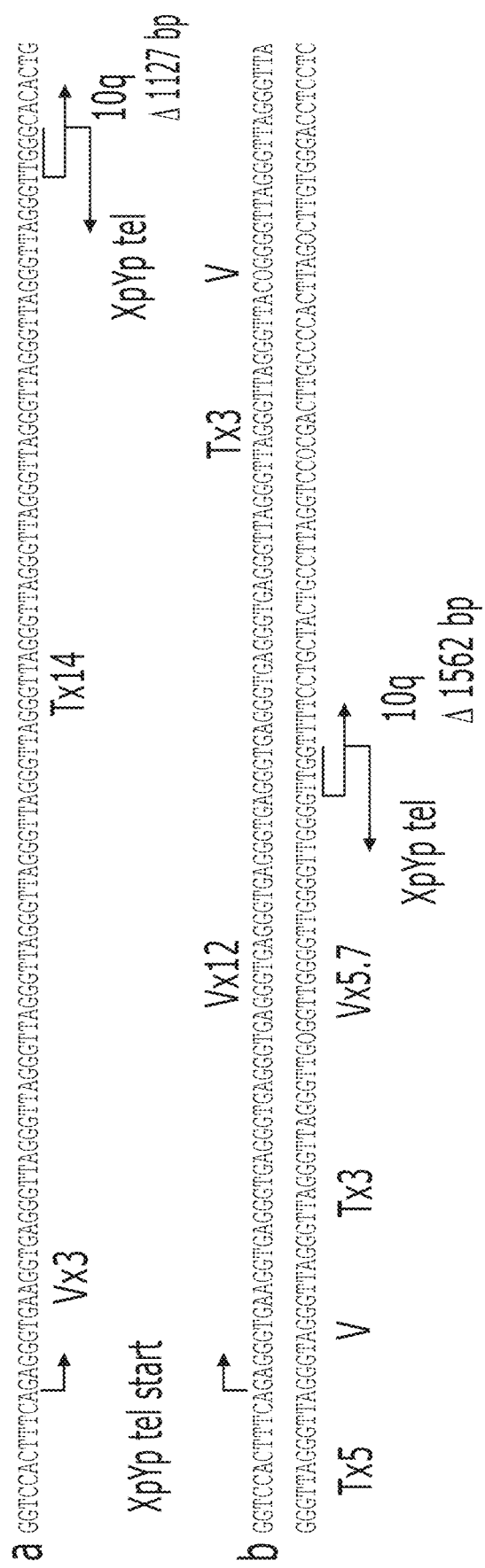
FIG. 1C shows examples of the DNA sequence of the fusion events highlighted in FIG. 1B; a is SEQ ID NO: 24 and b is SEQ ID NO:25. Arrows indicate the fusion junction, together with the participating telomere and the deletion from the start of the respective telomeres. Homology between the participating telomeres is underlined.
Figure 1D:
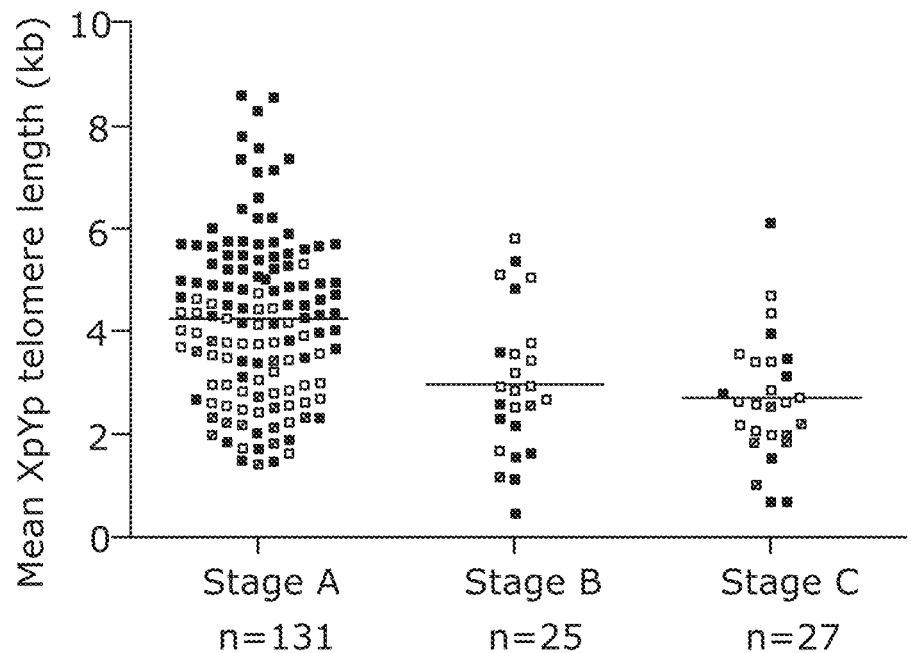
FIG. 1D shows mean XpYp telomere length data plotted as a function of Binet staging. Black squares indicate those that were not tested for fusion, empty squares those that were negative and marked squares those that were positive for fusion events.
Figure 1E:
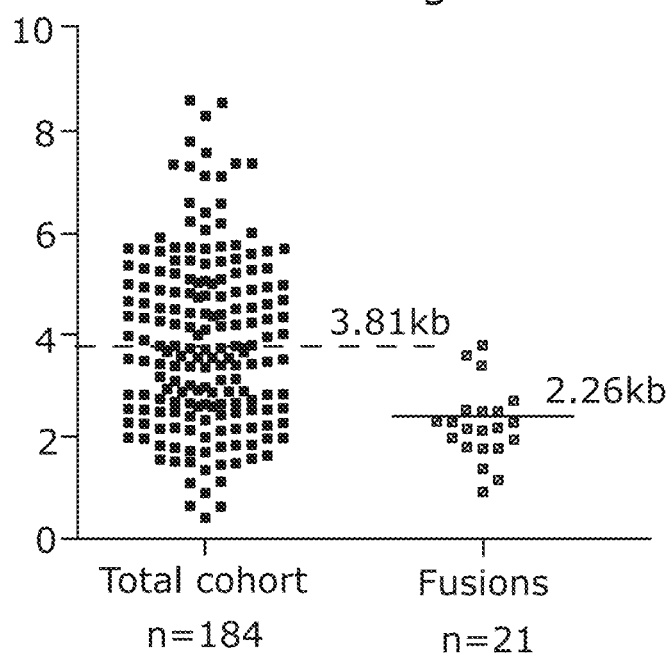
FIG. 1E shows telomere length data from the whole cohort, together with those that were positive for fusion events. The longest mean XpYp telomere (3.81 kb) in which fusion was detected is indicated with a dashed line and mean XpYp telomere length of the samples in which fusion was detected was 2.26 kb.

We analyzed the telomere length distribution in 184 CLL patients using single telomere length analysis (STELA) at the XpYp telomere (FIG. 1A). Given that we have previously shown that telomere end-end fusion events can be detected in CLL patients with short telomeres[15], we systematically looked for telomere fusions in the CLL samples with the shortest mean telomere lengths (n=88). We only considered a fusion event to be bone fide when it could be fully characterized by direct DNA sequence analysis (FIG. 1B, 1C). Telomere fusions were detectable in samples derived from all Binet stages, suggesting that they are not merely a characteristic of advanced disease (FIG. 1D; fusions marked in red). However, fusions were only detected in samples with a mean telomere length of ≤3.81 kb. We therefore used this telomere length as a threshold to define the upper limit of the 'fusogenic' range for our cohort using this chromosome. FIG. 1E shows that 98/184 (53.3%) of the CLL samples had a mean XpYp telomere length equal or less than 3.81 kb with a mean fusogenic telomere length of 2.26 kb. We therefore used 2.26 kb as a way of defining two subsets of CLL patient samples in our cohort and determined the prognostic value of this mean telomere length threshold in our cohort. A total of 33/184 (17.9%) of the samples had a mean telomere length ≤2.26 kb.

Telomere Dysfunction is Highly Prognostic in CLL

Figure 2A:
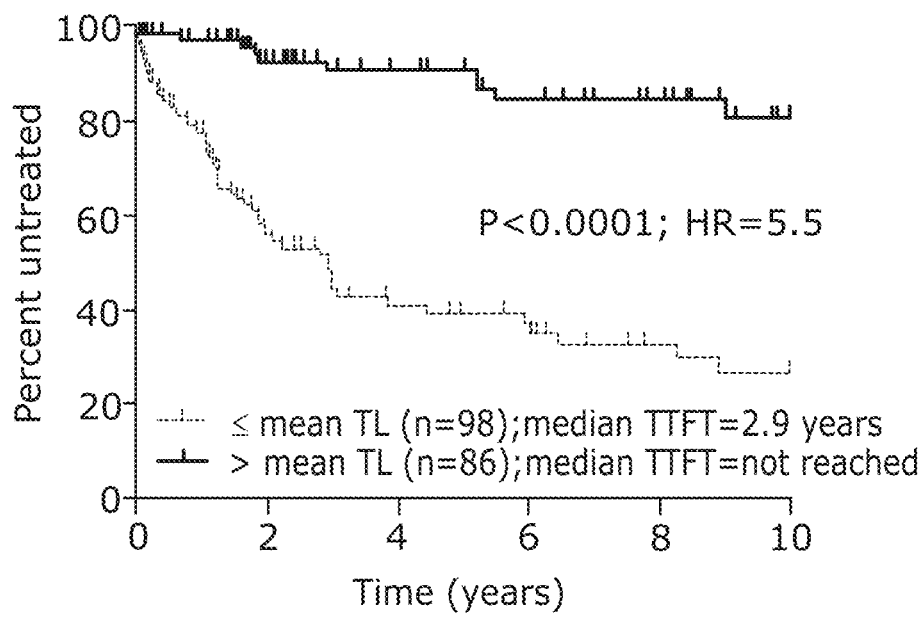
FIG. 2A illustrates prognostic value of mean telomere length, showing Kaplan Meier curves from the entire cohort for time to first treatment (TTFT). P values, Hazard Ratio (HR) are indicated on the plots together with numbers in each arm.
Figure 2B:
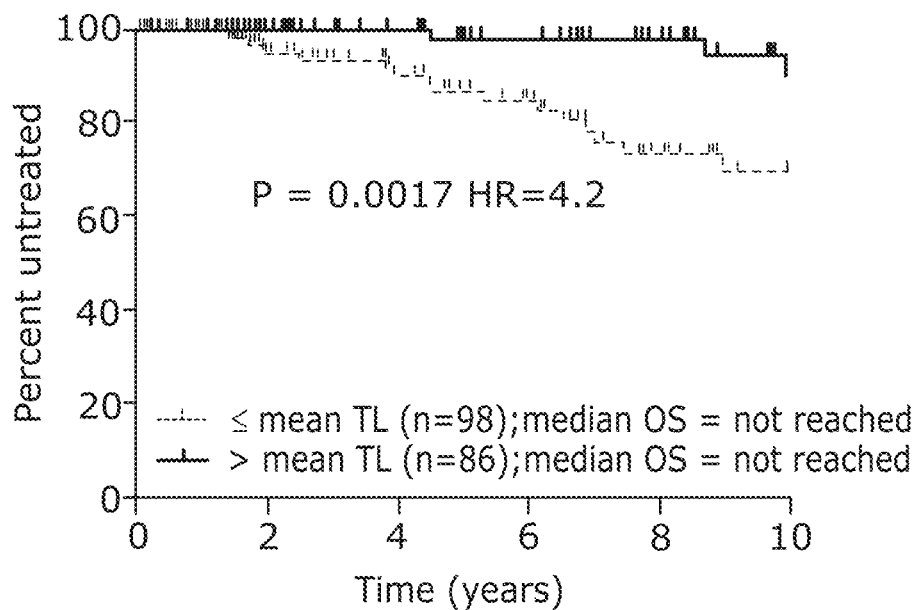
FIG. 2B shows Kaplan Meier curves from the entire cohort for overall survival (OS). P values, Hazard Ratio (HR) are indicated on the plots together with numbers in each arm.
Figure 3A:
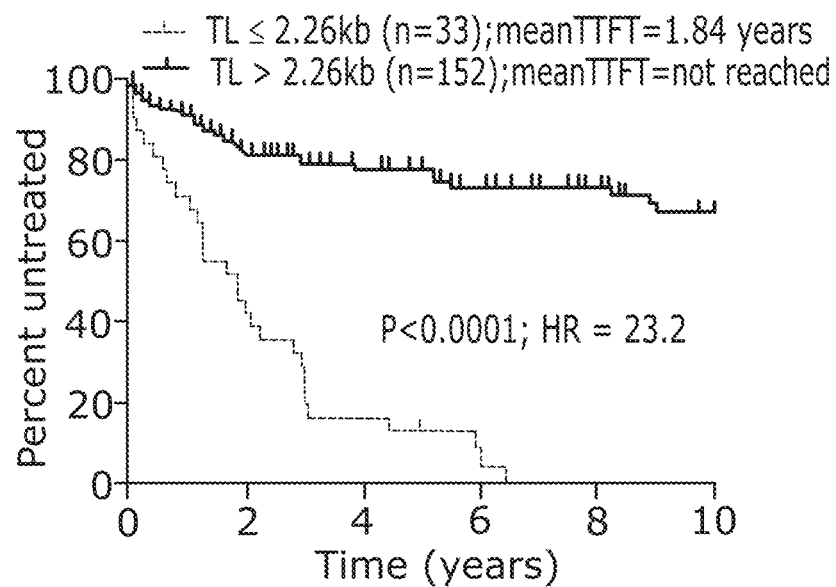
FIG. 3A illustrates prognostic value of telomere length as defined by fusion, showing Kaplan Meier curves from the entire cohort for time to first treatment (TFFT). P-values and Hazard Ratio (HR) are indicated on the plots, together with numbers in each arm.
Figure 3B:
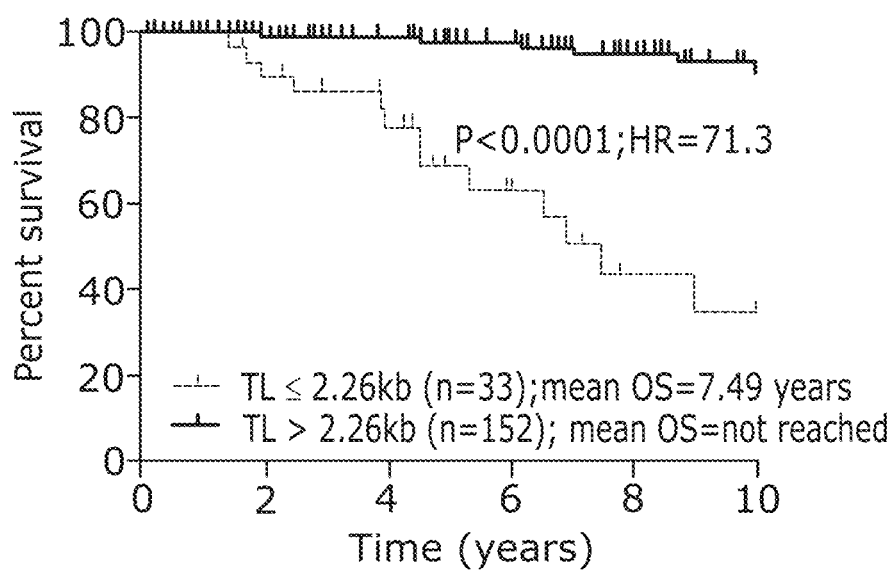
FIG. 3B shows Kaplan Meier curves from the entire cohort for mean survival (OS). P-values and Hazard Ratio (HR) are indicated on the plots, together with numbers in each arm.

In keeping with previous studies, mean telomere length was prognostic in our cohort of patients for TTFT (P<0.001; HR=5.5) and OS (p=0.0017; HR4.2) (FIG. 2). However, categorization of the samples based on telomere dysfunction (≤2.26 kb telomere length of the XpYp telomere) revealed remarkably enhanced prognostic discrimination. FIGS. 3A and 3B show that a mean telomere length ≤2.26 kb was highly prognostic for TTFT and OS. The median TTFT was 1.8 years (P<0.0001; HR=23.2) and the median OS was 7.5 years (P<0.0001; HR=71.3). In contrast, the median TTFT and OS were not reached in the longer telomere subset. Particularly striking was the impact of telomere length on OS in our cohort; the Kaplan Meier curve for patients with >2.26 kb telomere length showed almost no erosion over the 10 year follow-up period; 98% survival at 5 years and 96% survival at 10 years. Whereas, only 36% of the short telomere group was alive at the 10-year censor point indicating that patients with ≤2.26 kb were more than 70 times more likely to die in unit time. These data are summarised in Table-2.

Figure 3C:
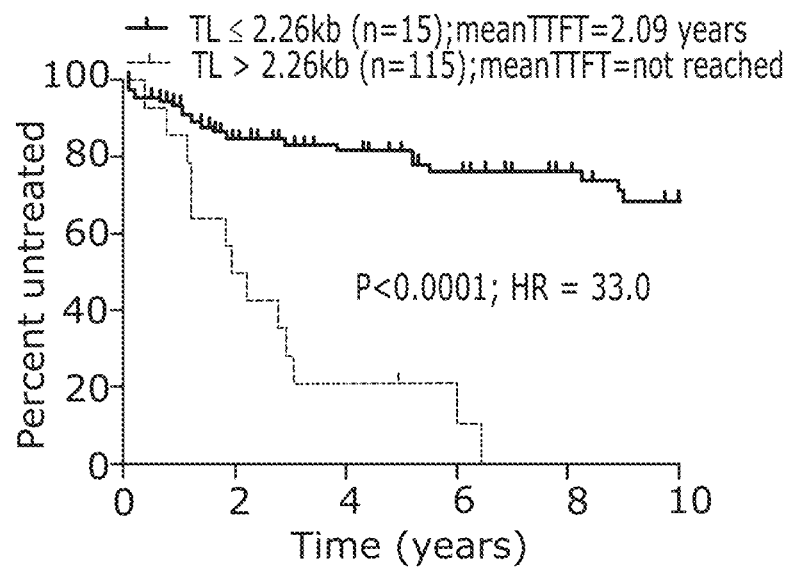
FIG. 3C shows Kaplan Meier curves from the Binet stage A only cohort for time to first treatment (TFFT).
Figure 3D:
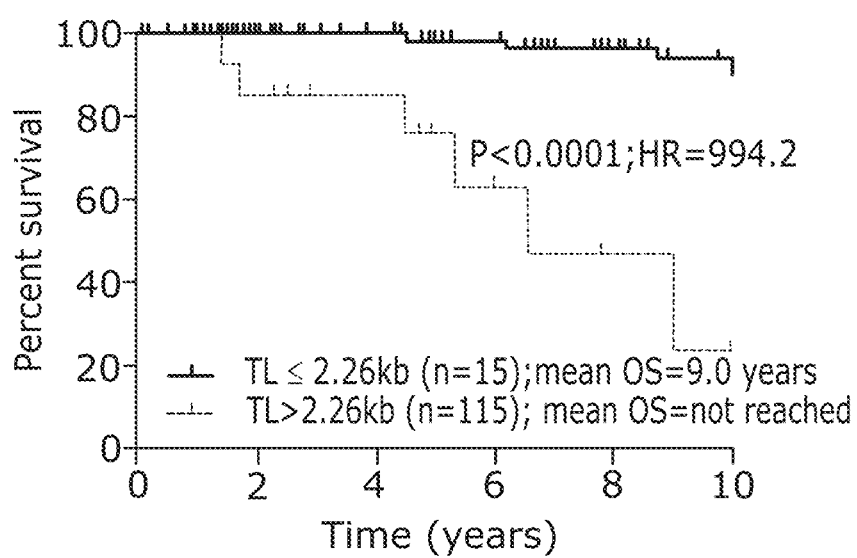
FIG. 3D shows shows Kaplan Meier curves from the Binet stage A only cohort for mean survival (OS).

Stage A patients with short telomeres have more aggressive disease Given that the majority of CLL patients present with early stage disease and this group represent the greatest challenge in terms of prognostication, we performed a subset analysis of only the Binet stage A patients. 130/184 (70.6%) of our cohort was Binet stage A at diagnosis of which 15 (11.5%) had ≤2.26 kb telomere length for the XpYp telomere. FIGS. 3C and 3D show the prognostic impact of short telomeres in early stage disease. The median TTFT was 2.1 years (P<0.0001; HR=33.0) and the median OS was 9.0 years (P<0.0001; HR=994.2). Once again, the median TTFT and OS were not reached in the longer telomere group. The remarkable hazard ratio for OS suggests that these patients are almost 1000 times more likely to succumb to their disease in unit time than patients with longer telomeres. Once again, the superior Kaplan Meier curve revealed that patients with longer telomeres had a survival rate of 96% at 10 years.

Figure 3E:
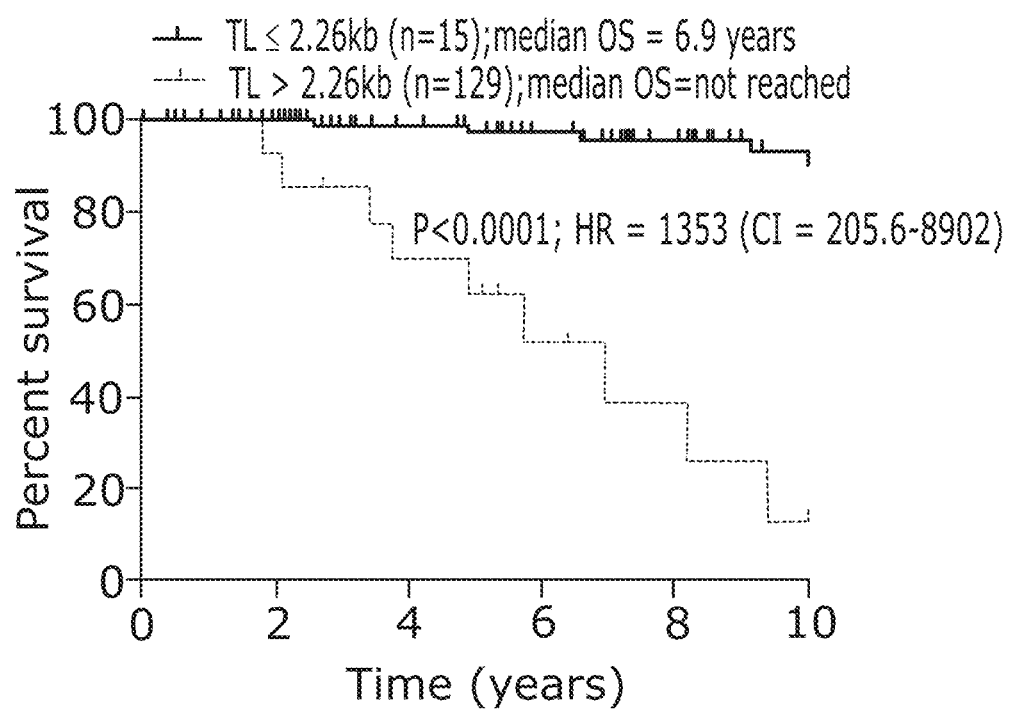
FIG. 3E shows Kaplan Meier curves from the entire cohort for median overall survival (OS). P-values and Hazard Ratio (HR) are indicated on the plots, together with numbers in each arm.

Expansion of the dataset to 144 Stage A patients, provided further verification that the specific telomere length of 2.26 kb provided the maximal prognostic power for this assay in CLL and the HR for overall survival increased to 1353 (FIG. 3E).

Recursive Partitioning Identifies the 2.26 kb Threshold as Most Prognostic for Survival Although we had experimentally determined the telomere length for telomere dysfunction in CLL and shown that this was highly prognostic, we wanted to establish if this represented the optimal telomere length cutoff for predicting survival in our cohort. By performing recursive partitioning on our data set, we found 2.26 kb represented the optimum telomere length, and was the most prognostic threshold for the total cohort and the Stage A cohort (FIG. 3E).

Figure 3F:
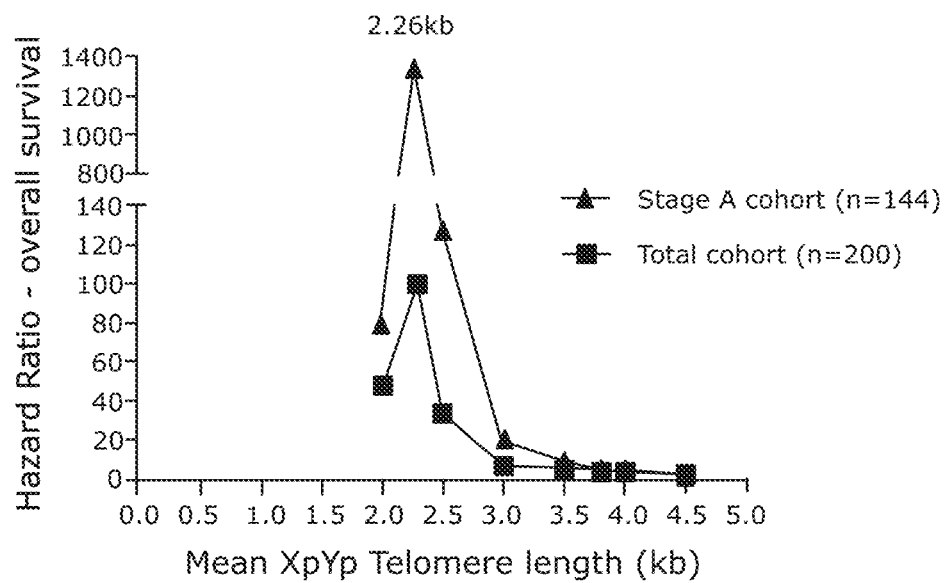
FIG. 3F illustrates recursive partitioning of the data set showing that 2.26 kb is the optimal telomere threshold as a prognostic tool for defining survival in the whole data set.
Figure 3G:
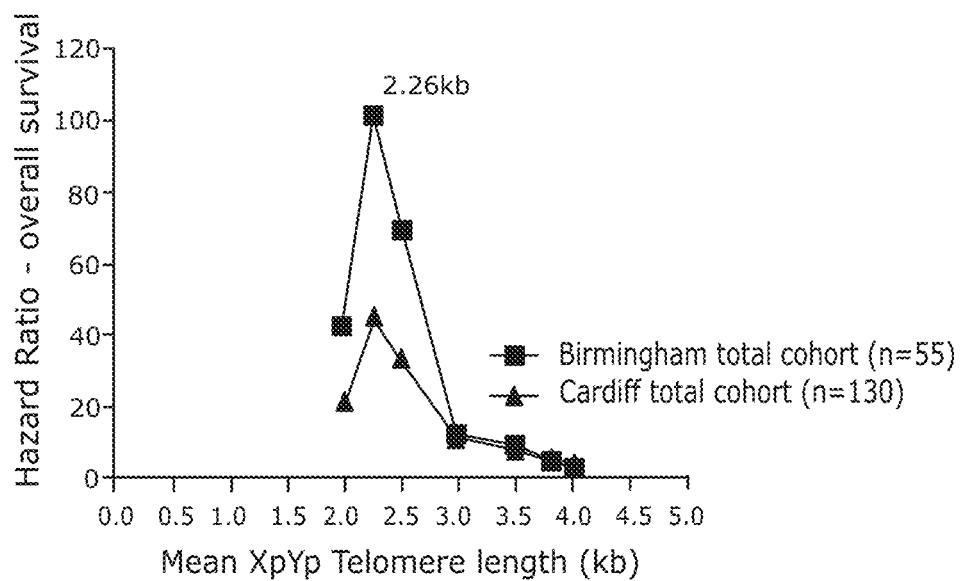
FIG. 3G illustrates recursive partitioning of the data set showing that 2.26 kb is the optimal telomere threshold as a prognostic tool for defining survival the 2 population cohorts.

Given that our cohort was made of samples derived from two different centers (Cardiff and Birmingham), we repeated the analysis in these two separate populations and derived essentially the same result (FIG. 3F). This approach provides further circumstantial evidence that 2.26 kb represents the biological limit of telomere stability and confirms the clinical importance of this mean fusogenic telomere length in CLL.

Figure 4A:
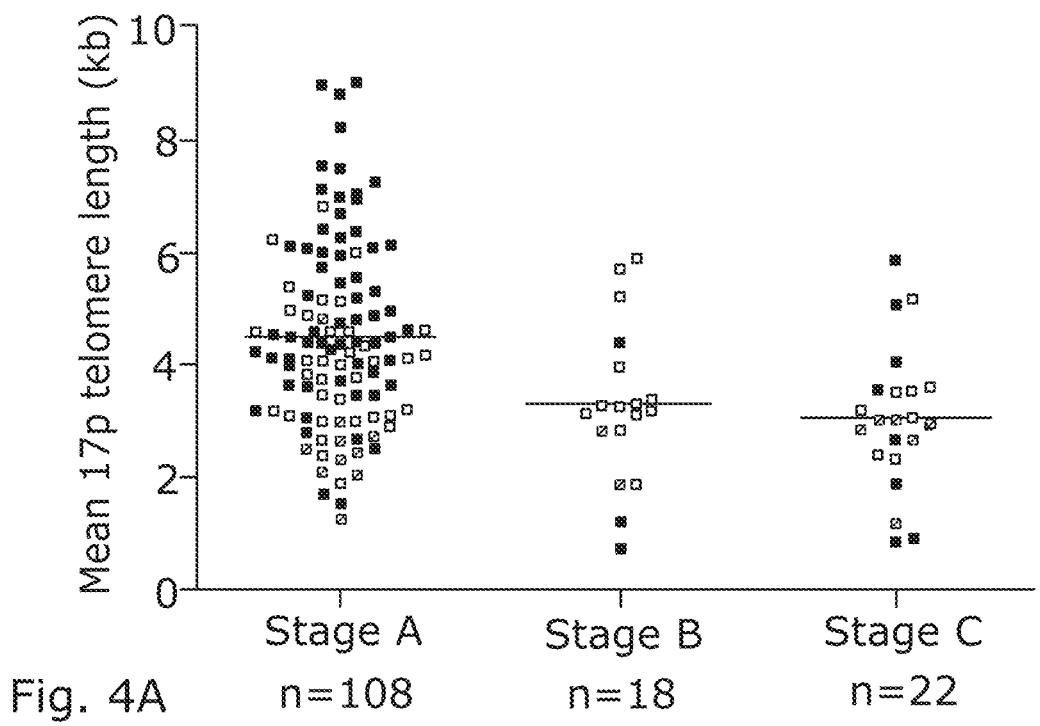
FIG. 4A shows mean 17p telomere length data plotted as a function of Binet staging. Black squares indicate those that were not tested for fusion, empty squares those that were negative and marked squares those that were positive for fusion events.
Figure 4B:
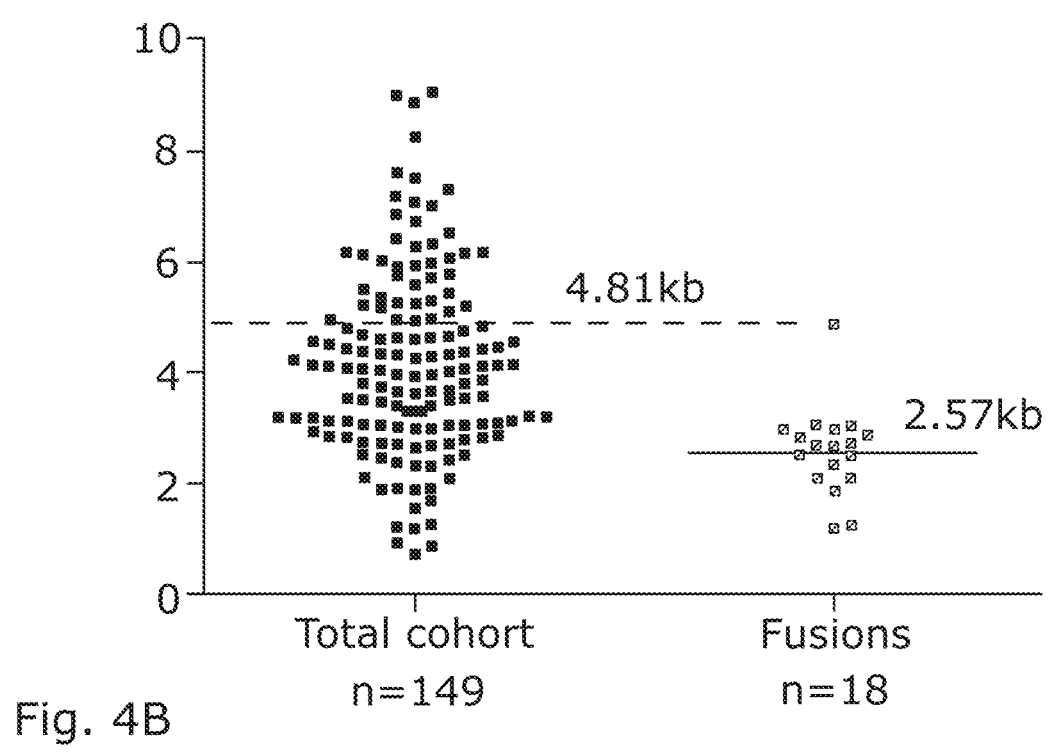
FIG. 4B shows telomere length data from the whole cohort, together with those that were positive for fusion events. The longest mean XpYp telomere (4.81 kb) in which fusion was detected is indicated with a dashed line and denotes the upper limit of the fusogenic range for the 17p telomere. The mean telomere length of the samples in which fusions could be detected was 2.57 kb.
Figure 4C:
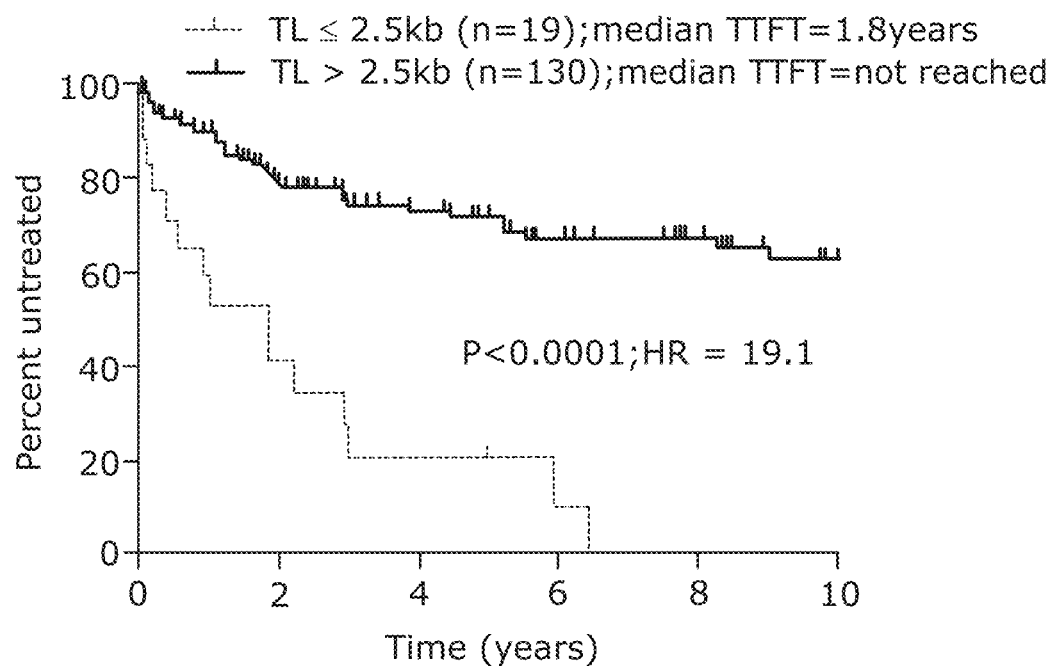
FIG. 4C shows Kaplan Meier curves for time to first treatment based on a cut-off of 2.5 kb derived from recursive partitioning of the data.
Figure 4D:
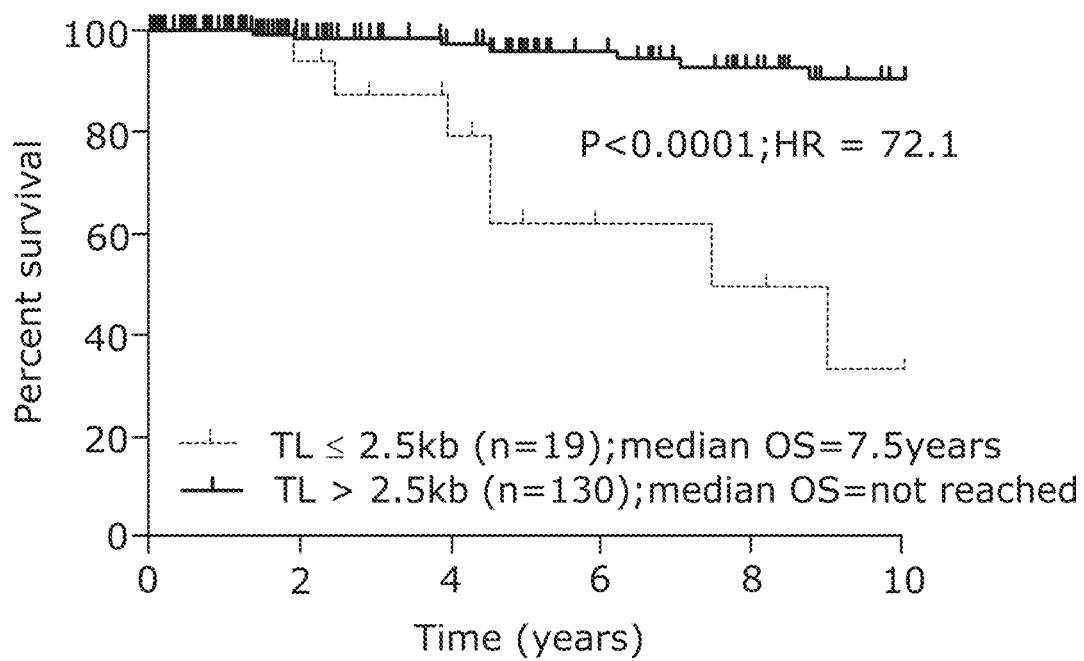
FIG. 4D shows Kaplan Meier curves for overall survival based on a cut-off of 2.5 kb derived from recursive partitioning of the data.
Figure 4E:
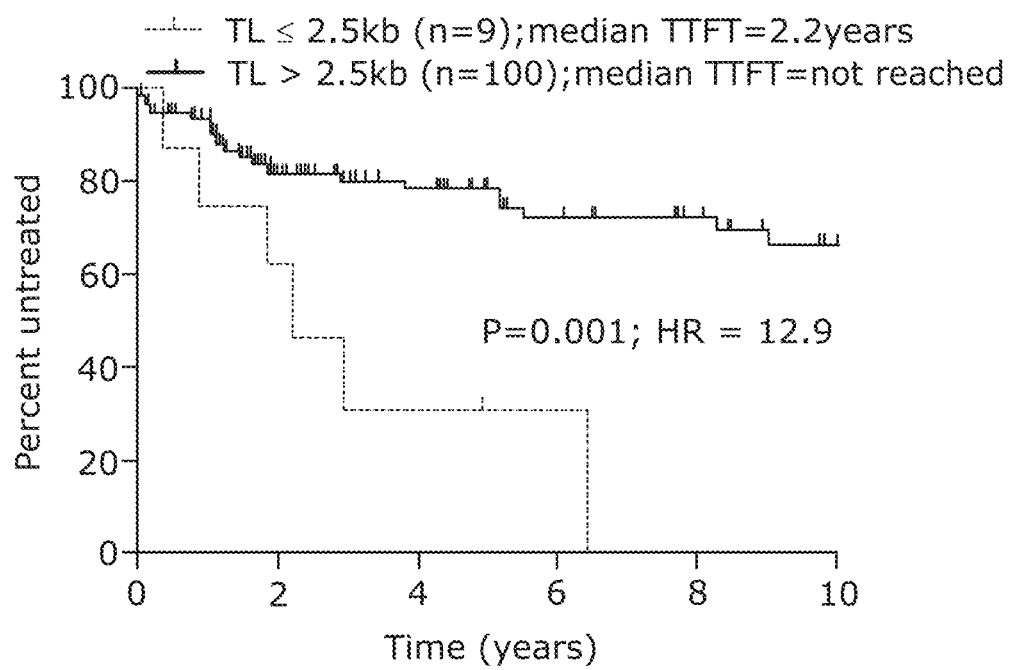
FIG. 4E shows Kaplan Meier curves for time to first treatment for stage A patients only based on a cut-off of 2.5 kb derived from recursive partitioning of the data.
Figure 4F:
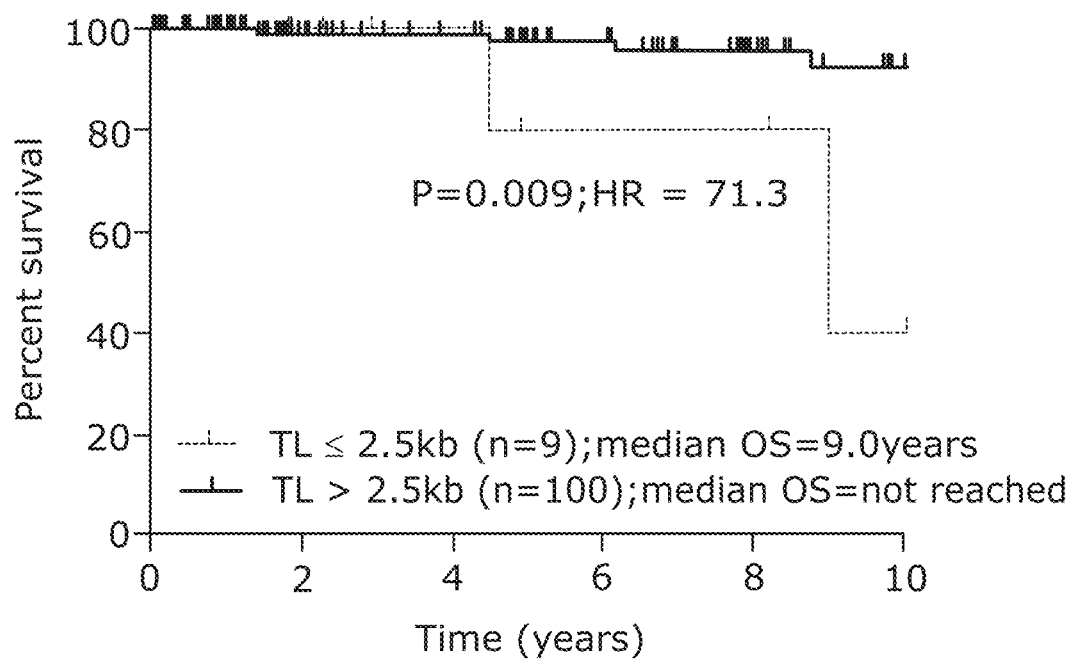
FIG. 4F shows Kaplan Meier curves for overall survival for stage A patients only based on a cut-off of 2.5 kb derived from recursive partitioning of the data.
Figure 4G:
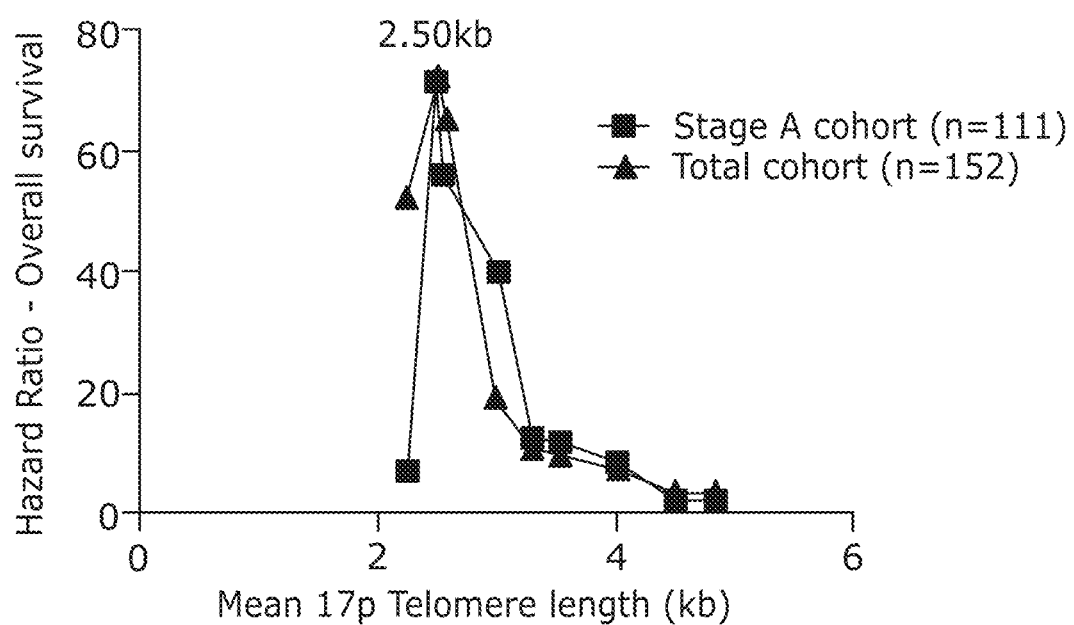
FIG. 4G shows a plot of mean telomere length of the 17p telomere versus hazard ratios for overall survival. Recursive partitioning illustrates that 2.5 kb is the optimal threshold for defining prognosis using this telomere.
Figure 5A:
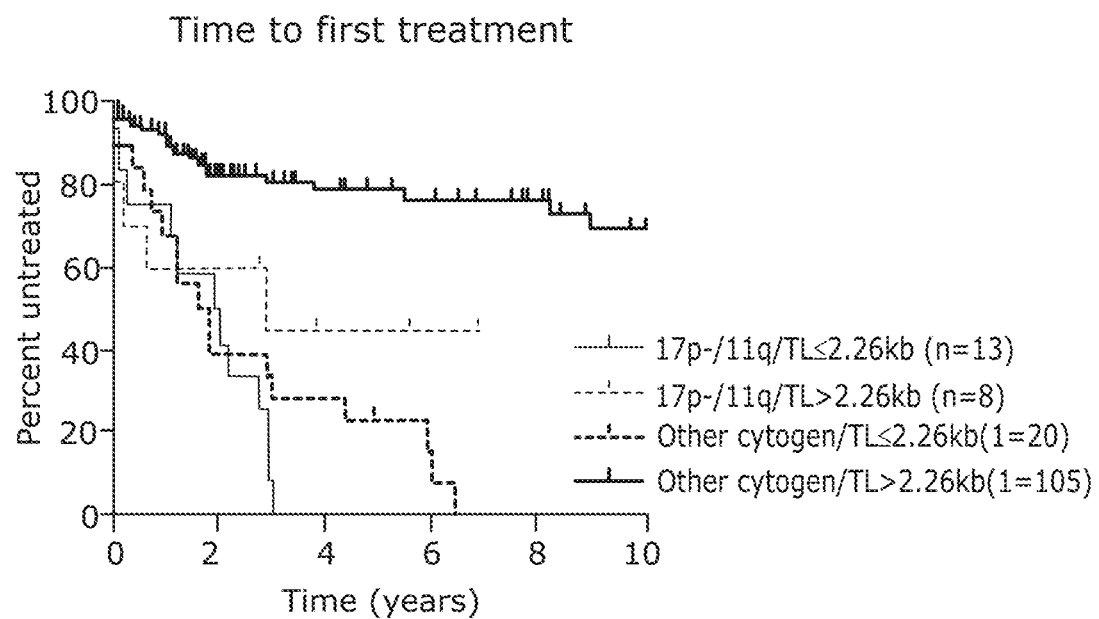
FIG. 5A illustrates superiority of telomere length compared to other known prognostic parameters, showing Kaplan Meier curves with telomere length compared to cytogenetics.
Figure 5B:
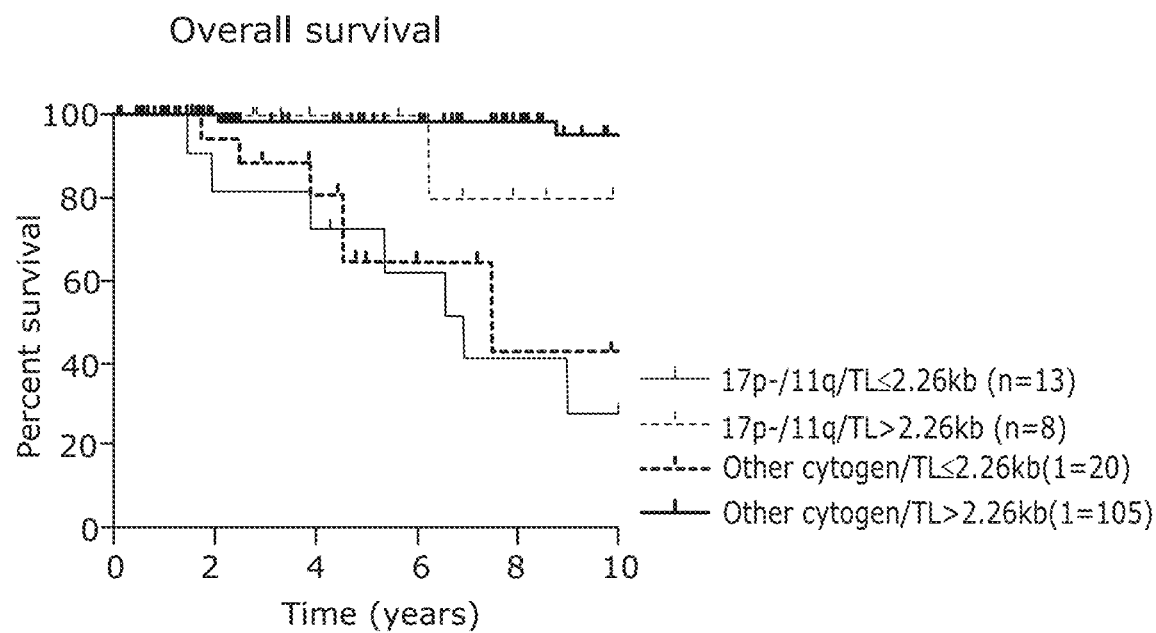
FIG. 5B shows Kaplan Meier curves with telomere length compared to cytogenetics.
Figure 5C:
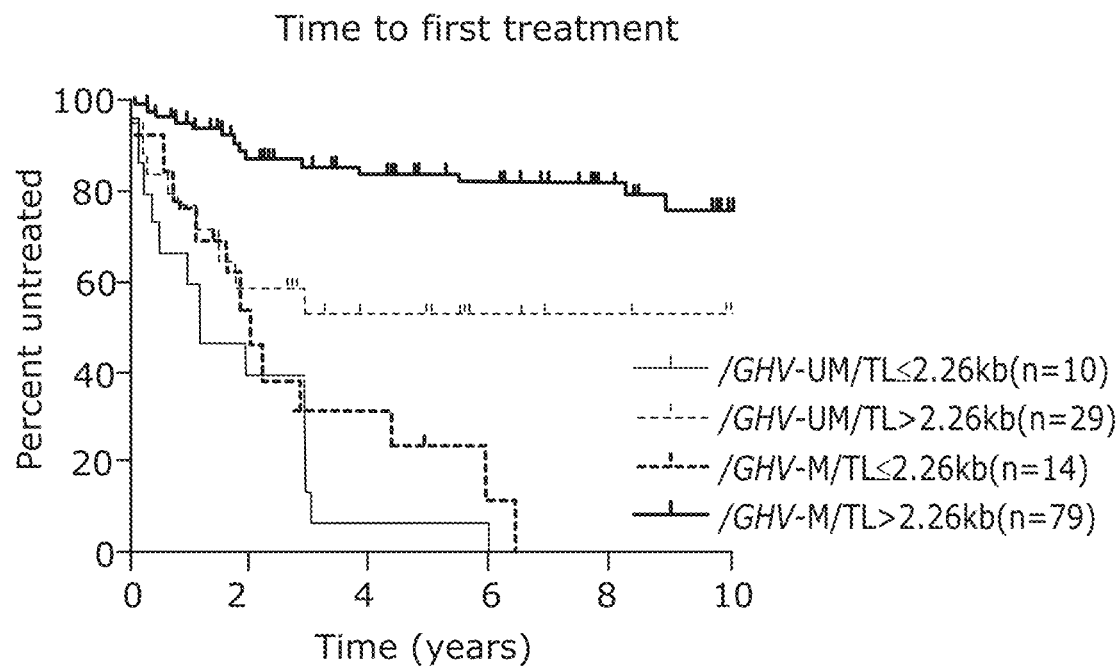
FIG. 5C shows Kaplan Meier curves with telomere length compared to IGHV status as a function of TFFT.
Figure 5D:
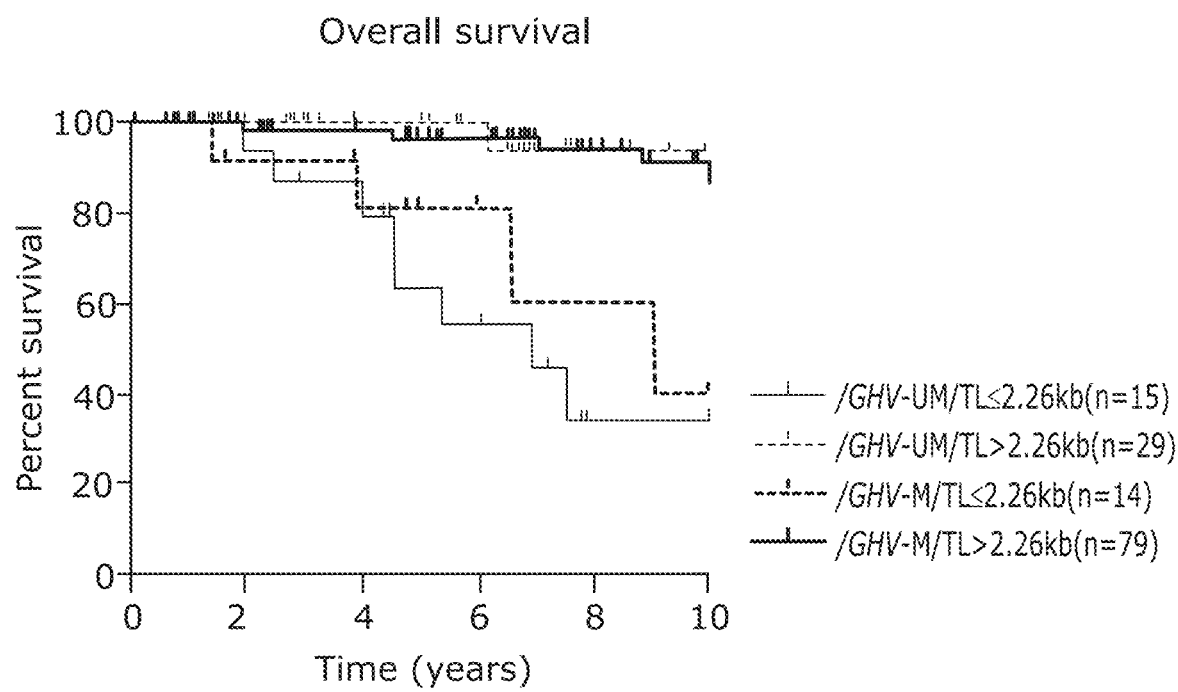
FIG. 5D shows Kaplan Meier curves with telomere length compared to IGHV status as a function of OS.
Figure 5E:
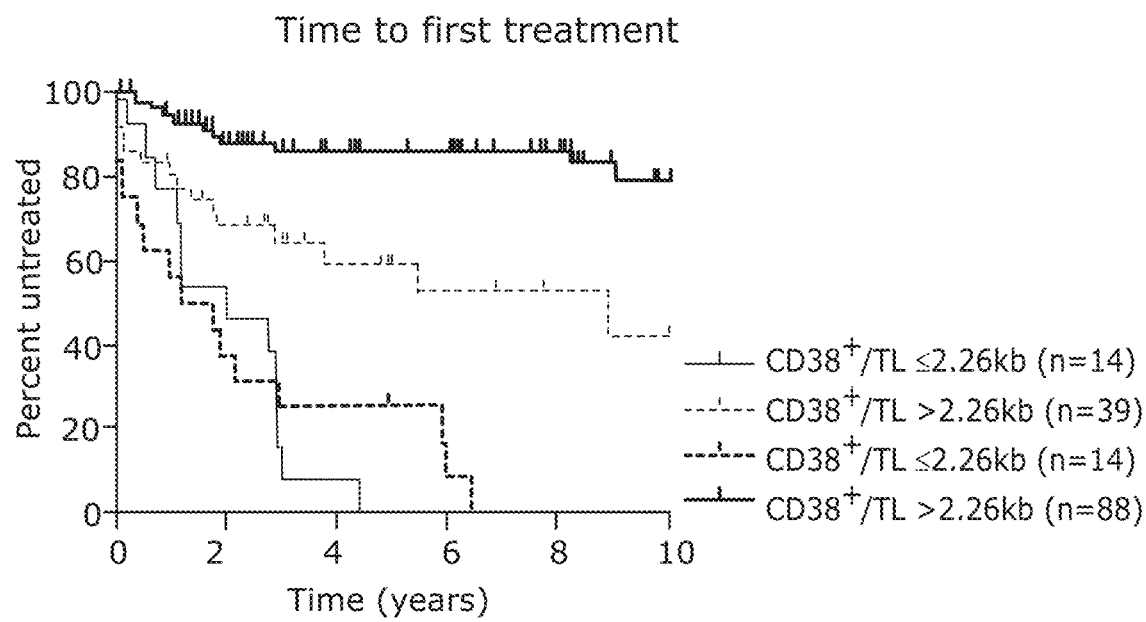
FIG. 5E shows Kaplan Meier curves with telomere length compared to CD38 status as a function of TFFT.
Figure 5F:
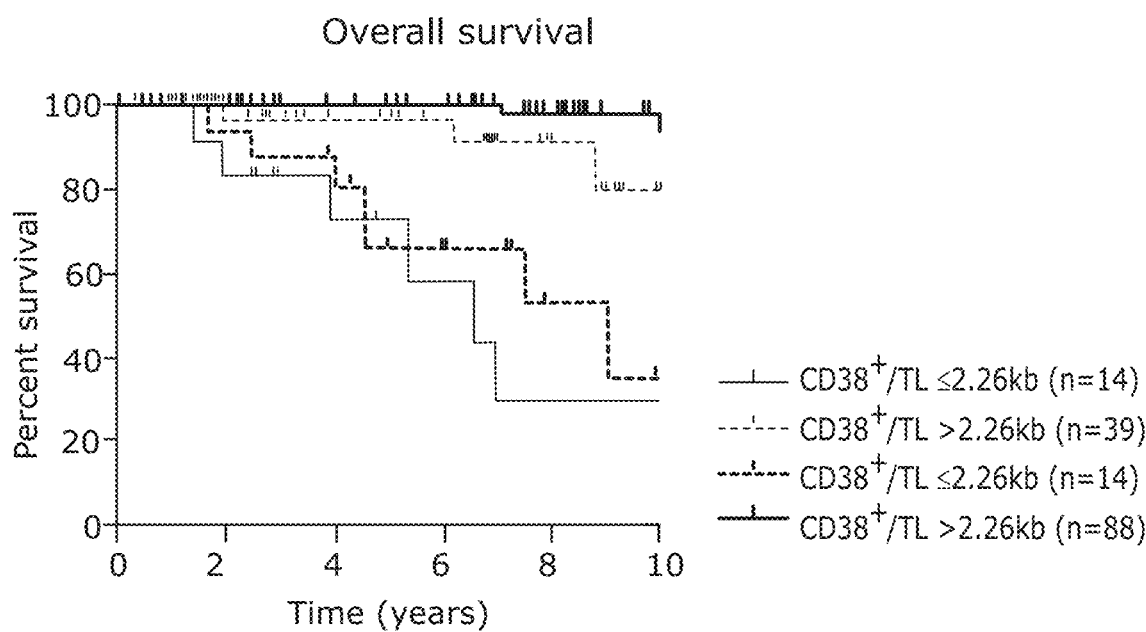
FIG. 5F shows Kaplan Meier curves with telomere length compared to CD38 status as a function of OS.
Figure 5G:
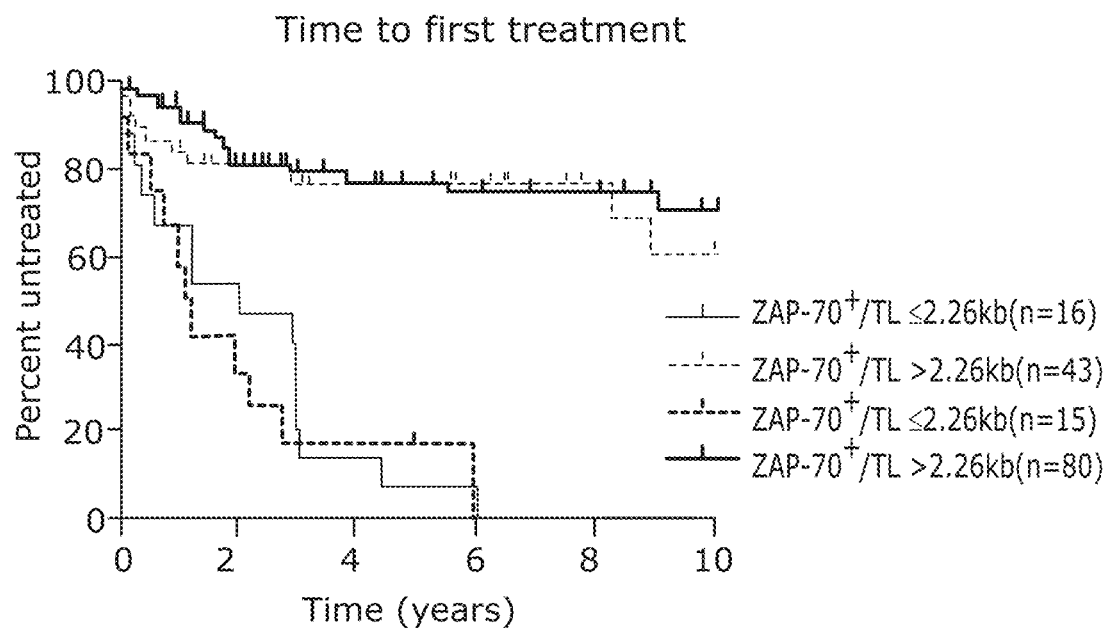
FIG. 5G shows Kaplan Meier curves with telomere length compared to CD38 status as a function of TFFT.
Figure 5H:
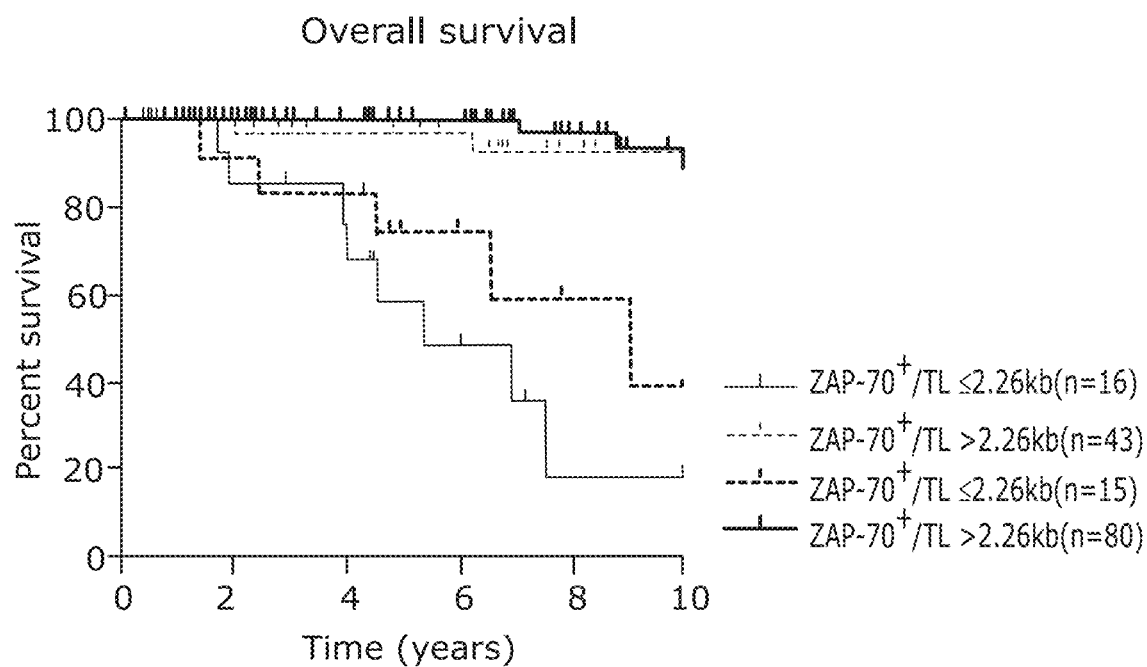
FIG. 5H shows Kaplan Meier curves with telomere length compared to CD38 status as a function of OS.

We considered that this mean fusogenic telomere length may be conserved at other chromosome ends and thus we analyzed telomere length at 17p (FIG. 4A) in 149/184 (81%) of the patient cohort. The mean 17p telomere length of the samples in which we could detect fusions was similar to that observed at XpYp (2.57 kb, ±0.79, P=0.21; FIG. 4B). Recursive partitioning revealed the optimal telomere length for determining prognosis was 2.5 kb; this was highly prognostic in the whole cohort (OS P<0.0001, HR=72) and stage A patients (OS P=0.009, HR=71, FIG. 4C-G).

Telomere Length is Superior to Other Prognostic Parameters

We next investigated the impact of dysfunctional telomeres on other known prognostic markers in CLL, including cytogenetics, IGHV mutation status, CD38 expression, ZAP-70 expression and Beta-2 microglobulin (β2M). The combined analysis of telomere length with FISH cytogenetics, IGHV mutation status, CD38 expression, ZAP-70 expression are shown in FIG. 5. As shown, short telomere length defines poor prognostic subsets of patients within cytogenetic risk groups, IGHV unmutated and mutated groups, CD38$^+$ and CD38$^-$ groups, ZAP-70$^+$ and ZAP-70$^-$ groups and β2M high and low groups, in terms of TTFT and OS. Combining these markers with telomere length enhanced the prognostic power still further; for example, the analysis of the concordant datasets revealed that high CD38 expression in conjunction with telomere length ≤2.26 kb yielded a HR of 2915 (P<0.0001, Table-4).

Telomere Length is the Dominant Co-Variable in Multivariate Analysis

In multivariate analysis forward selection identified telomere dysfunction (≤2.26 kb) as the most significant parameter for TTFT (HR=4.2; CI 1.9-8.8, P=0.0002) and OS (HR=10.9; CI 3.8-31.2, P<0.0001). Only IGHV mutation status and Binet stage retained independent prognostic significance as co-variables in the model for TTFT and only CD38 in terms of OS. It is of particular interest that IGHV mutation status and 'high-risk' cytogenetics were not independently prognostic in terms of OS. To our knowledge, this is the first time that these parameters have failed to prove significant for OS in this disease.

Telomere Length Defines Response to Treatment in CLL

Figure 6:
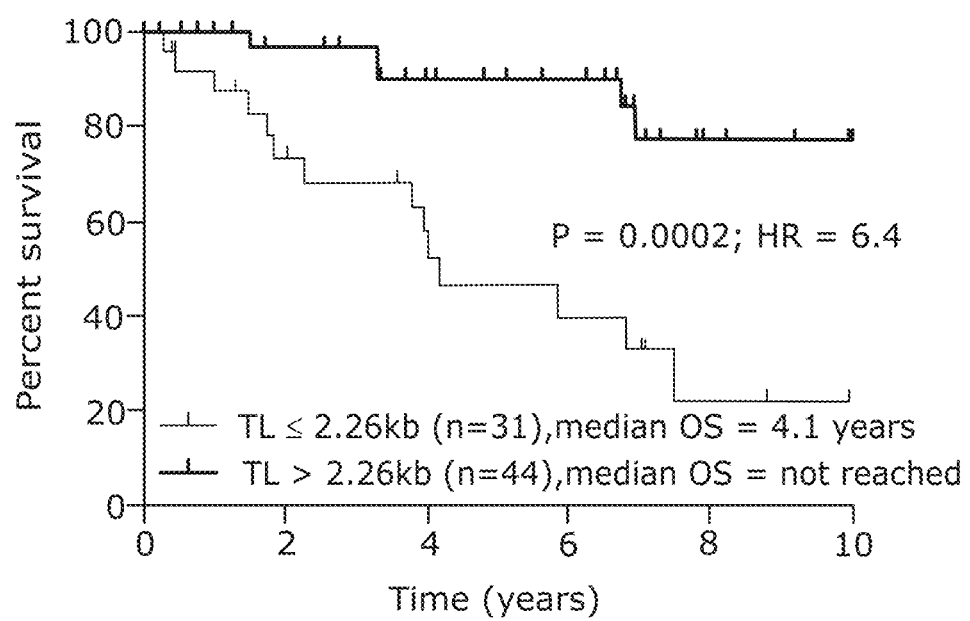
FIG. 6 shows that the telomere threshold of 2.26 kb, derived from the XpYp chromosome, is highly prognostic for CLL patient response to treatment. Kaplan Meier curves for a subset of patients with CLL that received treatment (n=75). Survival time was calculated from time of first treatment. P-values and Hazard Ratio (HR) are indicated on the plots, together with numbers in each arm.

Given that we have shown that telomere length provides powerful prognostic information in CLL, we further considered that telomere length may also provide information about the ability of patients to respond to treatment. We therefore undertook a subset analysis (n=75) of our CLL patient cohort for those that had received treatment. Telomere length was highly prognostic for response to treatment with a HR of 6.4 (P=0.0002) (FIG. 6).

Telomeric Parameters Defined in CLL are Prognostic in Other Indications.

Figure 7A:
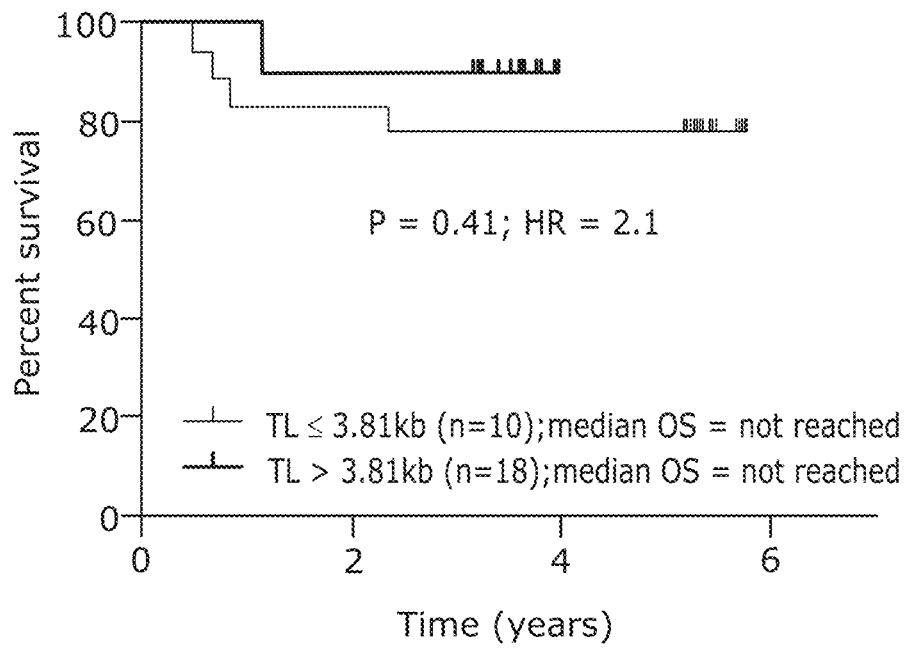
FIG. 7A illustrates that telomere length (TL), as defined by fusion, is also prognostic in breast cancer, showing Kaplan Meier curves from the entire cohort for a TL of 3.81 kb, for overall survival. P-values and Hazard Ratio (HR) are indicated on the plots, together with numbers in each arm.
Figure 7B:
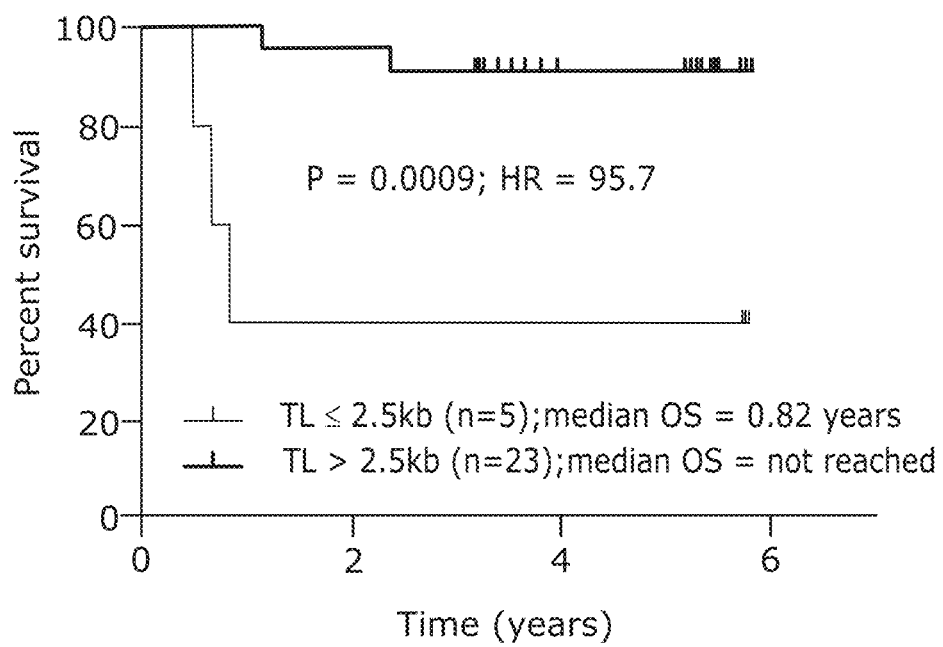
FIG. 7B illustrates that telomere length (TL), as defined by fusion, is also prognostic in breast cancer, showing Kaplan Meier curves from the entire cohort for a TL of 2.5 kb, for overall survival. P-values and Hazard Ratio (HR) are indicated on the plots, together with numbers in each arm.
Figure 7C:
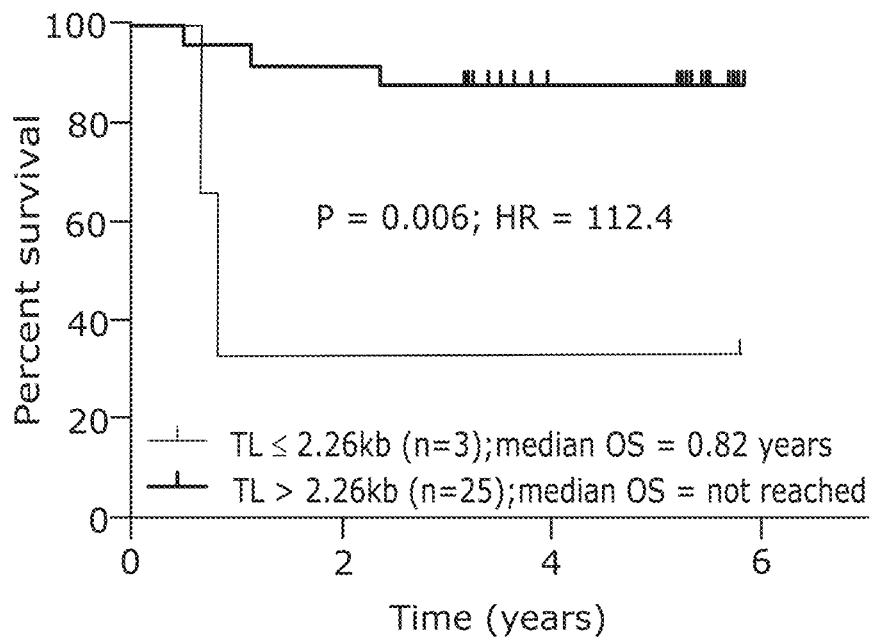
FIG. 7C illustrates that telomere length (TL), as defined by fusion, is also prognostic in breast cancer, showing Kaplan Meier curves from the entire cohort for a TL of 2.26 kb, for overall survival. P-values and Hazard Ratio (HR) are indicated on the plots, together with numbers in each arm.
Figure 7D:
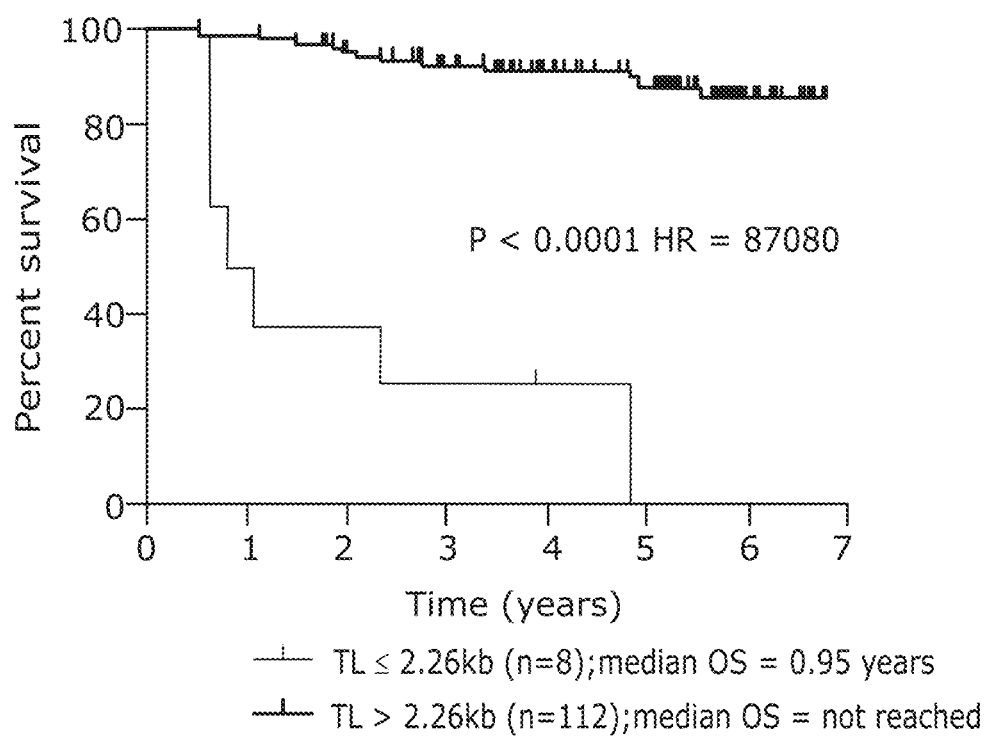
FIG. 7D illustrates that telomere length (TL), as defined by fusion, is also prognostic in breast cancer, showing Kaplan Meier curves from the entire cohort for a TL of 2.26 kb, for overall survival. P-values and Hazard Ratio (HR) are indicated on the plots, together with numbers in each arm.

We examined a cohort of 28 patients with invasive ductal carcinoma of the breast. We analyzed XpYp telomere length using STELA and categorized the patients based on the 2.26 kb telomere length cutoff defined in CLL. Despite a limited follow up period of 4.6 years, the 2.26 kb mean fusogenic telomere length provided remarkable levels of prognostication for overall survival in this disease with a hazard ratio of 112 (P=0.0056), and a median survival in the poor prognostic group of 301 days (FIG. 7A-C). Expansion of the dataset to 120 breast cancer patients, provided further verification that the specific telomere length of 2.26 kb provided the maximal prognostic power for this assay in breast cancer and the HR for overall survival increased to 87080 (FIG. 7D).

Figure 7E:
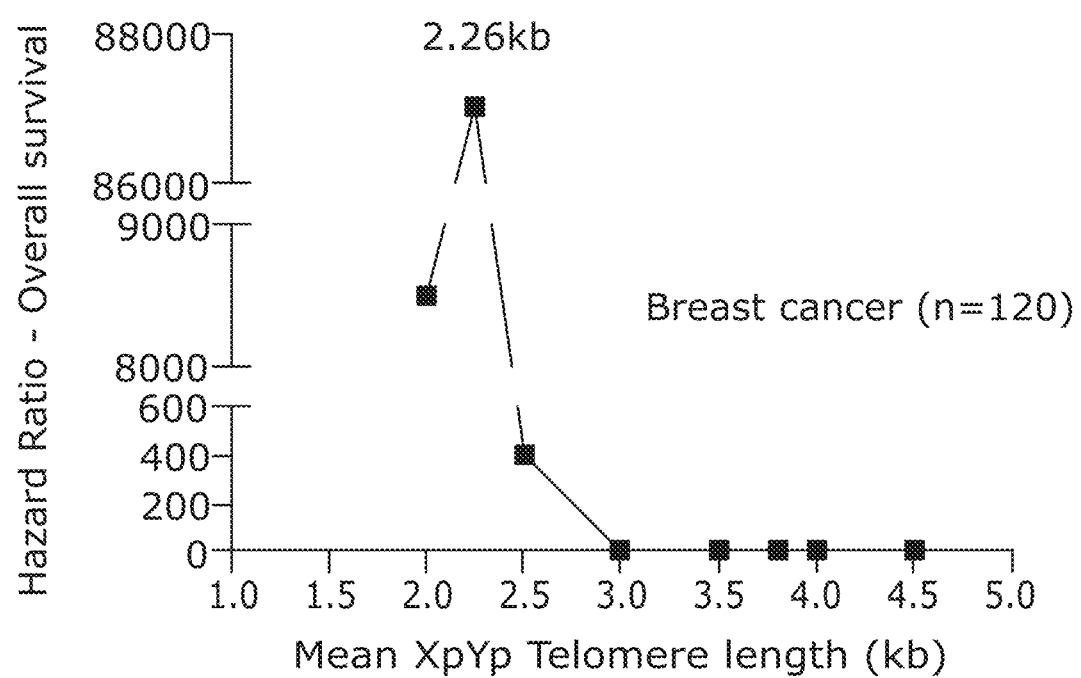
FIG. 7E shows by recursive partitioning of the data set that 2.26 kb is the optimal telomere threshold as a prognostic tool for defining survival in the whole data set.

As with CLL, recursive partitioning of the Breast Cancer Cohort data showed that the optimum telomere length as defined by HR was 2.26 kb (FIG. 7E).

Figure 8A:
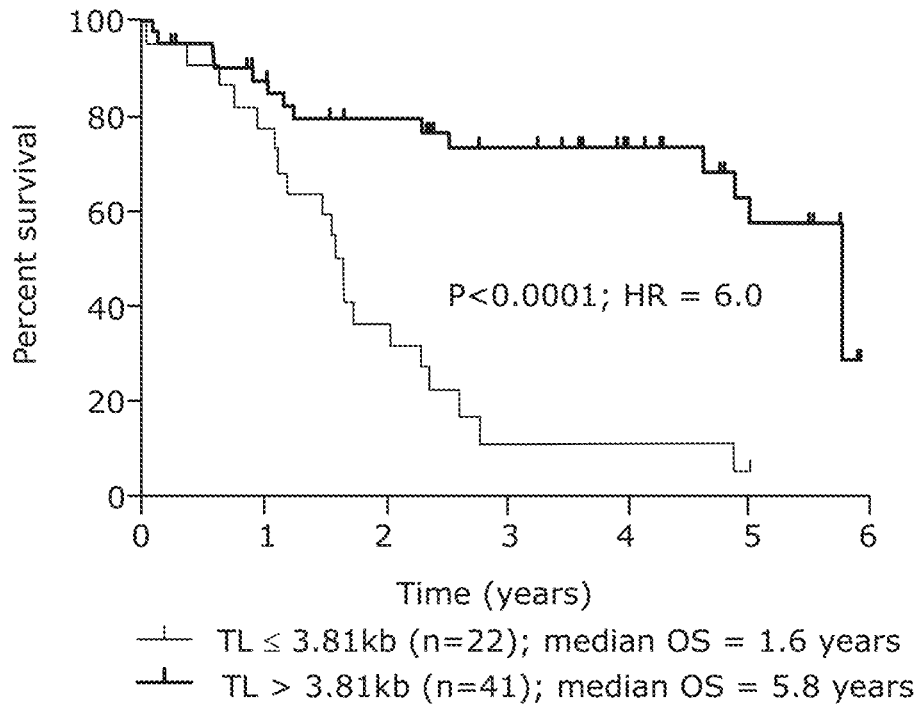
FIG. 8A shows Kaplan Meier curves from the entire cohort, for overall survival in MDS for a TL of 3.81 kb. P-values and Hazard Ratio (HR) are indicated on the plots, together with numbers in each arm.
Figure 8B:
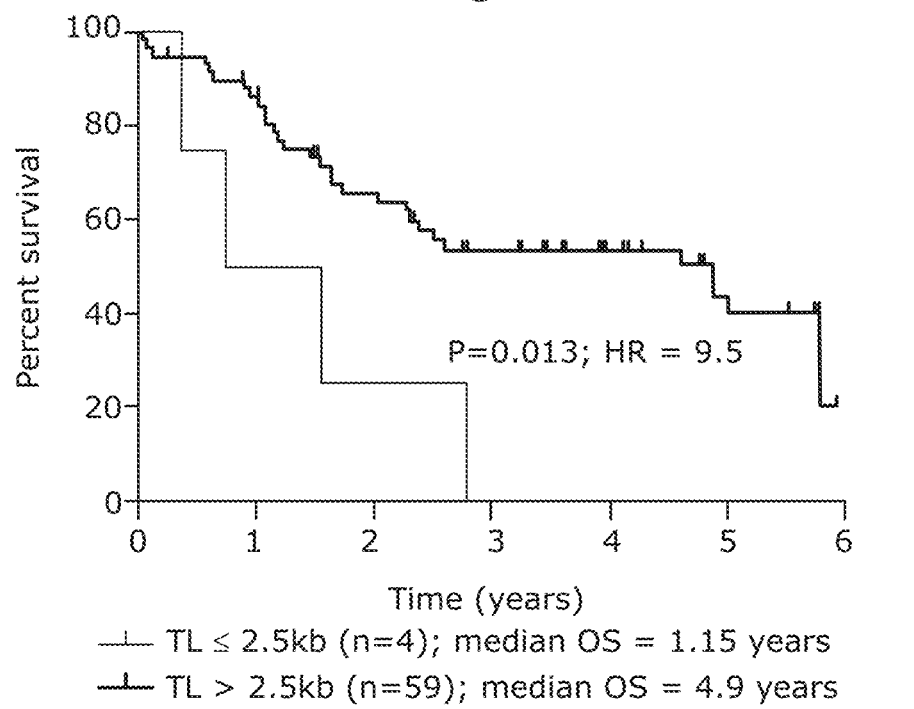
FIG. 8B shows Kaplan Meier curves from the entire cohort, for overall survival in MDS for a TL of 2.5 kb. P-values and Hazard Ratio (HR) are indicated on the plots, together with numbers in each arm.
Figure 8C:
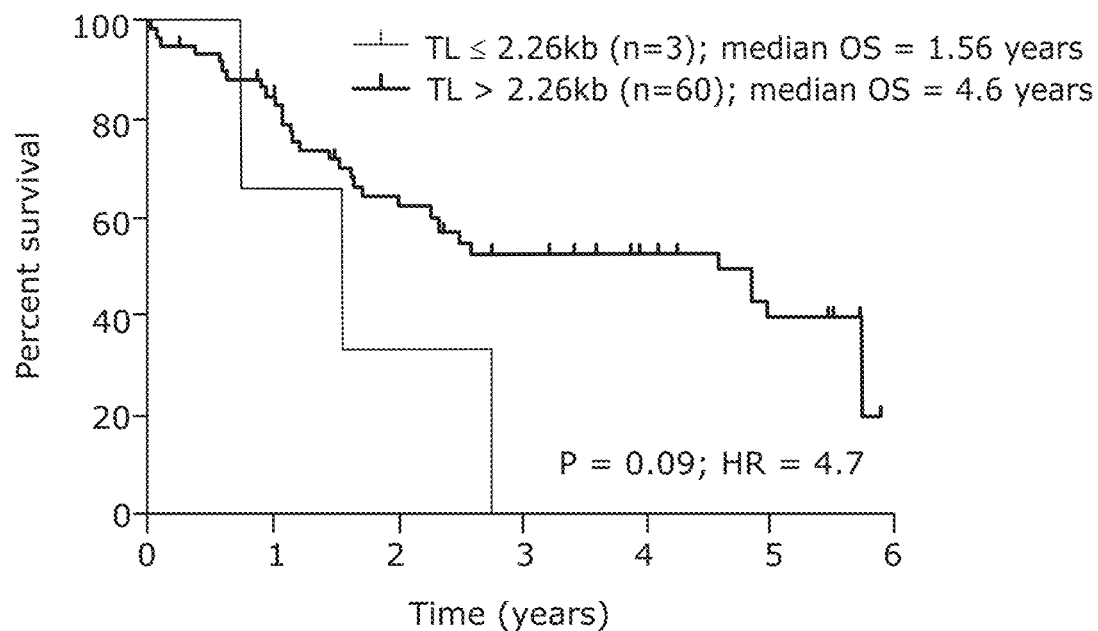
FIG. 8C shows Kaplan Meier curves from the entire cohort, for overall survival in MDS for a TL of 2.26 kb. P-values and Hazard Ratio (HR) are indicated on the plots, together with numbers in each arm.
Figure 8D:
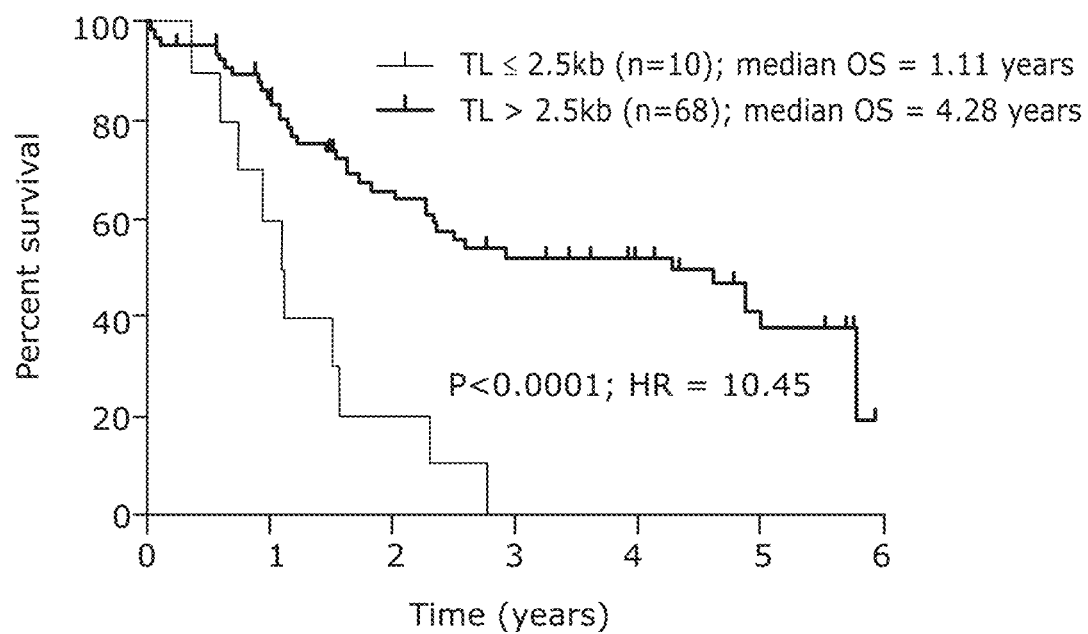
FIG. 8D shows that the 2.5 kb telomere threshold offers better prognostic power in MDS.
Figure 8E:
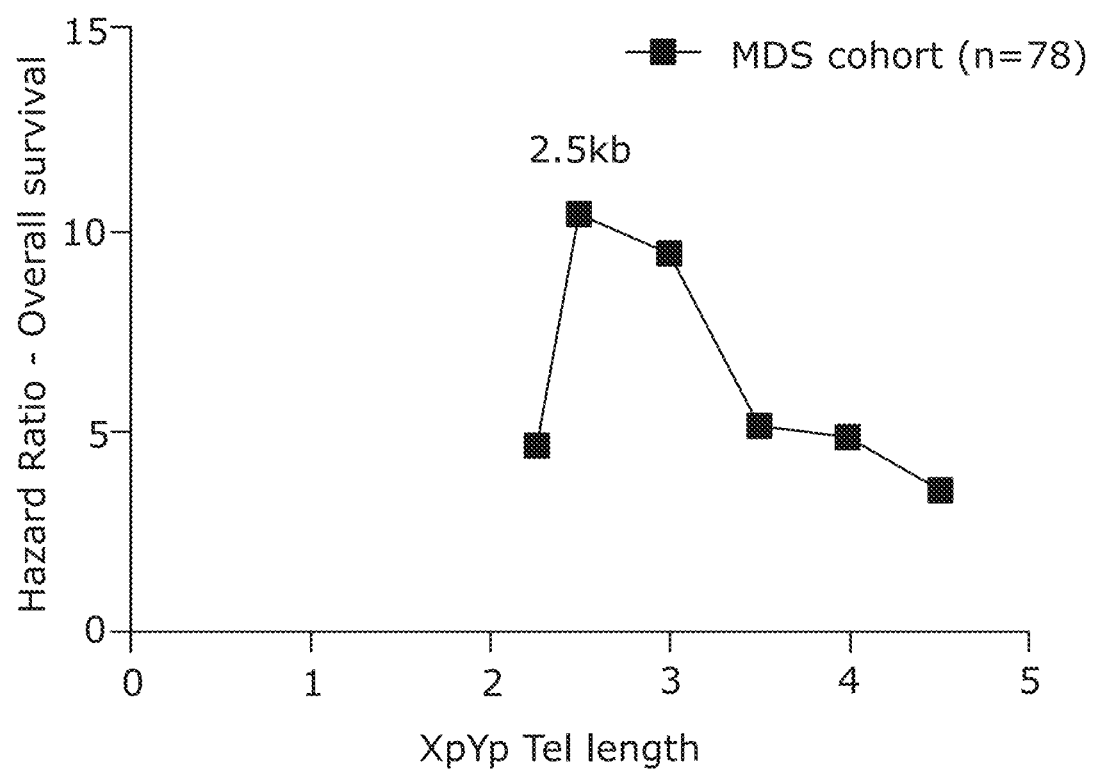
FIG. 8E shows by recursive partitioning of the data set that 2.5 kb is the optimal telomere threshold as a prognostic tool for defining survival in the whole data set for MDS.

We also examined telomere length in MDS using STELA and used the mean fusogenic telomere length defined in CLL to provide prognostic information in MDS. We analysed a panel of 63 MDS patients for which we had survival data. The 2.26 kb mean fusogenic telomere length as defined in CLL, provided some prognostic power in MDS with a HR of 4.7 (P=0.09) for overall survival (FIG. 8A-C). Unlike the CLL and breast cancer samples, the MDS samples were not purified and contained varying unidentified proportions of unaffected cells. We considered that the presence of unaffected normal cells would skew the optimal telomere length threshold for prognostication in this cohort. This was apparent from the recursive partitioning, where the optimal telomere length was 2.5 kb (HR=9.5, P=0.026) a difference of just 240 bp (FIG. 8E). Expansion of the dataset to 78 MDS patients provided further verification that the specific telomere length of 2.5 kb provided the maximal prognostic power of this assay in MDS and the HR for overall survival increased to 10.45 (FIG. 7D). Purification of MDS cells using CD34 may improve the accuracy of telomere-based prognostication in MDS.

STELA at 7q and XpYp

Figure 9:
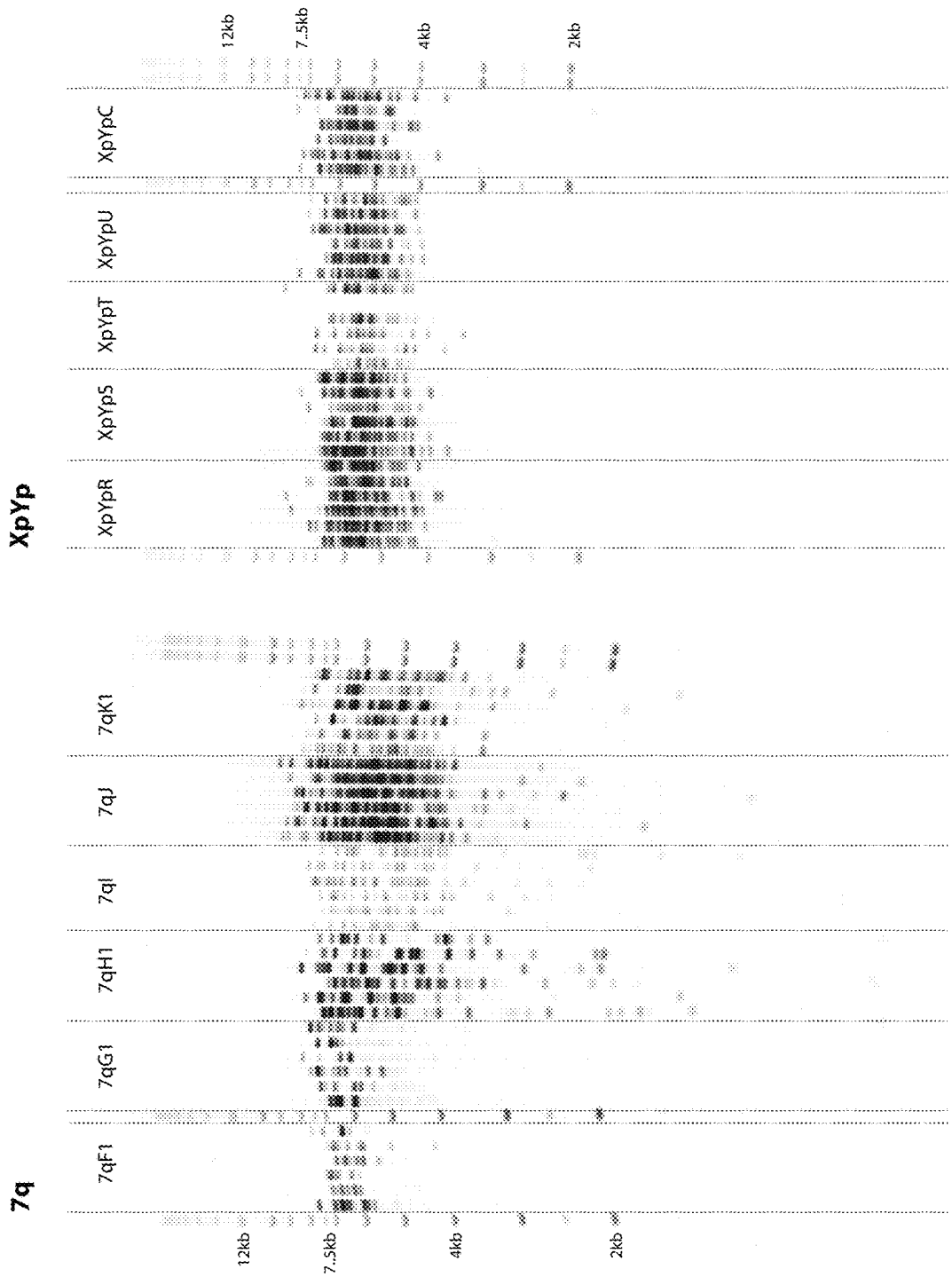
FIG. 9 shows development of Single Telomere Length Analysis (STELA) assays at 7q and XpYp. Primers were designed around telomere-specific nucleotides for both the 7q and XpYp chromosome ends using DNA extracted from a clonal population of a fibrosarcoma cell line (HT1080 clone 2).

We further developed STELA at the 7q and XpYp telomeres. To do this we identified unique sub-telomeric DNA sequences and used these to design the oligonucleotide primers (7qF1, 7qG1, 7qH1, 7q1, 7qJ, 7qK1, XpYpR, XpYpS, XpYpT and XpYpU) that would allow for specific analysis of the 7q and XpYp telomeres. We tested these primers with STELA using DNA derived from a clonal population of HT1080 fibrosarcoma cells and compared the telomere length distributions to that generated with XpYpC (FIG. 9). As a clonal cell line these cells are expected to exhibit a relatively homogeneous telomere length distributions. The data shown in FIG. 9, indicated that all the primers tested were capable of telomeric amplification, generating telomere length profiles consistent with the amplification of specific telomeres. However it was also apparent that some primers were more efficient, both in terms of single-molecule efficiency and PCR efficiency. With for example, 7qF1 and 7qG1 producing a more homogeneous profiles than 7qH, 7qI, 7qJ and 7qK1 and with for example, XpYpR generating a larger number of amplifiable molecules each with a more intense hybridization signal compared to those generated with XpYpT or XpYpU. These data indicate that these primers have both higher single-molecule PCR efficiencies and PCR amplification efficiencies. These indicate that these primers and other primers unique to these sub-telomeric sequences can provide robust telomere length profile using the STELA methodology.

SUMMARY

The main findings of this study can be summarised as follows:

Telomere length analysis, as defined by telomere dysfunction, provides a highly prognostic tool in human diseases, such as CLL and other human malignancies, permitting considerable discrimination for clinical outcome following treatment. Prognostic power should enable clinicians to confidently predict the clinical course of these heterogeneous diseases.

Moreover, telomere dysfunction provides remarkable prognostic resolution in early disease stage.

Only telomeres in the lower portion of the length distribution profile have the propensity for end-end fusion; using the XpYp chromosome a telomere length of ≤2.26 kb is a mean fusogenic telomere length for telomere dysfunction in a primary human tumor, below which patients of human malignancies show poor prognostic outcome. Using a number of chromosomes a telomere length ≤2.69 kb is a predictor for telomere dysfunction.

Patients with XpYp telomeres longer than 2.26 kb have remarkably stable and indolent disease (98% of these patients were alive at 5 years and 96% at the 10-year censor point).

Consistent telomere analysis in MDS and breast cancer shows that high-resolution telomere length analysis is likely to be highly prognostic in other haematological malignancies but importantly also in solid tumours.

By applying a telomere length threshold based on telomere dysfunction, this transforms the prognostic power of telomere analysis into the most prognostic parameter ever described in both univariate and multivariate analysis.

REFERENCES

1. Jiang H, Ju Z, Rudolph K L. Telomere shortening and ageing. Z. Gerontol Geriat 2007; 40:314-324.
2. Gertler R, Rosenberg R, Stricker D, et al. Telomere length and human telomerase reverse transcriptase expression as markers for progression and prognosis of colorectal carcinoma. J Clin Oncol 2004; 22:1807-14.
3. Meeker A K, Argani P. Telomere shortening occurs early during breast tumorigenesis: a cause of chromosome destabilization underlying malignant transformation? J Mammary Gland Biol Neoplasia 2004; 9:285-96.
4. Damle R N, Batliwalla F M, Ghiotto F, et al. Telomere length and telomerase activity delineate distinctive replicative features of the B-CLL subgroups defined by immunoglobulin V gene mutations. Blood 2004; 103:375-82.
5. Grabowski P, Hultdin M, Karlsson K, et al. Telomere length as a prognostic parameter in chronic lymphocytic leukemia with special reference to VH gene mutation status. Blood 2005; 105:4807-12.
6. Rossi D, Lobetti Bodoni C, Genuardi E, et al. Telomere length is an independent predictor of survival, treatment requirement and Richter's syndrome transformation in chronic lymphocytic leukemia. Leukemia 2009; 23:1062-72.
7. Sellmann L, de Beer D, Bartels M, et al. Telomeres and prognosis in patients with chronic lymphocytic leukaemia. Int J Hematol 2011; 93:74-82.
8. Roos G, Krober A, Grabowski P, et al. Short telomeres are associated with genetic complexity, high risk genomic aberrations, and short survival in chronic lymphocytic leukemia. Blood 2008; 111:2246-52.
9. Ricca I, Rocci A, Drandi D, et al. Telomere length identifies two different prognostic subgroups among VH-unmutated B-cell chronic lymphocytic leukemia patients. Leukemia 2007; 21:697-705.
10. Chin K, de Solorzano C O, Knowles D, et al. In situ analyses of genome instability in breast cancer. Nat Genet. 2004; 36:984-8.
11. Heaphy C M, Baumgartner K B, Bisoffi M, Baumgartner R N, Griffith J K. Telomere DNA content predicts breast cancer-free survival interval. Clin Cancer Res. 2007; 13:7037-43.
12. Lu L, Zhang C, Zhu G, et al. Telomerase Expression and Telomere Length in Breast Cancer and their Associations with Adjuvant Treatment and Disease Outcome. Breast Cancer Res. 2011; 13:R56.
13. Aubert G, Hills M, Lansdorp P M. Telomere length measurement-Caveats and a critical assessment of the available technologies and tools. Mutat Res. 2011 Jun. 8 [Epib ahead of print].
14. Baird D M. New developments in telomere length analysis. Exp Gerontol. 2005; 40:363-8.
15. Lin T T, Letsolo B T, Jones R E, et al. Telomere dysfunction and fusion during the progression of chronic lymphocytic leukaemia: evidence for a telomere crisis. Blood 2010; 116:1899-907.
16. Capper R, Britt-Compton B, Tankimanova M, et al. The nature of telomere fusion and a definition of the critical telomere length in human cells. Genes Dev. 2007; 21:2495-508.
17. Letsolo B T, Rowson J, Baird D M. Fusion of short telomeres in human cells is characterised by extensive deletion and microhomology and can result in complex rearrangements. Nucleic Acids Res. 2010; 38:1841-52.
18. Cawthon, R. M. Telomere measurement by quantitative PCR. Nucleic Acids Res. 2002; 30; e47.
19. Shen, J., Terry, M. B., Gurvich, I., Liao, Y., Senie, R. T. and Santella, R. M. Short telomere length and breast cancer risk: a study in sister sets. Cancer Res. 2007; 67: 5538-5544. Reviewed in Aviv, A. The epidemiology of human telomeres: faults and promises. J Gerontol A Biol Sci Med Sci, 2008; 63: 979-983.
20. Baird D M, Rowson J, Wynford-Thomas D, Kipling D. Extensive allelic variation and ultrashort telomeres in senescent human cells. Nat Genet. 2003; 33:203-7.
21. Britt-Compton B, Rowson J, Locke M, Mackenzie I, Kipling D, Baird D M. Structural stability and chromosome-specific telomere length is governed by cis-acting determinants in humans. Hum Mol Genet. 2006; 15:725-33.
22. Baird D M, Britt-Compton B, Rowson J, Amso N N, Gregory L, Kipling D. Telomere instability in the male germline. Hum Mol Genet. 2006; 15:45-51.

23. Britt-Compton B, Capper R, Rowson J, Baird D M. Short telomeres are preferentially elongated by telomerase in human cells. FEBS Lett 2009; 583:3076-80.
24. Binet J L, Auquier A, Dighiero G, et al. A new prognostic classification of chronic lymphocytic leukemia derived from a multivariate survival analysis. Cancer 1981; 48: 198-206.
25. Hewamana S, Alghazal S, Lin T T, et al. The N F-kappaB subunit Rel A is associated with in vitro survival and clinical disease progression in chronic lymphocytic leukemia and represents a promising therapeutic target. Blood 2008; 111:4681-9.
26. Sambrook J, Fritsh E F, Maniatis T. Molecular cloning: a laboratory manual. 2nd Edition ed. New York: Cold spring harbour laboratory press; 1989.

TABLE 1

Upper limit and mean telomere length at which telomere end-end fusion events can be detected for five different chromosome ends.

| Chromosome end | Upper limit (kb) | Mean of fusogenic range (kb) |
|---|---|---|
| XpYp | 3.81 | 2.26 |
| 17p | 4.81 | 2.57 |
| 2p | 5.01 | 3.01 |
| 16p | 4.49 | 2.94 |
| 18q | 4.47 | 2.66 |
| Mean ± SD | 4.52 ± 0.46 | 2.69 ± 0.30 |

TABLE 2

Comparison of prognostic factors in univariate analysis in terms of time to first treatment and overall survival

| Parameter | Time to first treatment | | | Overall survival | | |
| --- | --- | --- | --- | --- | --- | --- |
| | Median (years) | HR (95% CI) | P-value | Median (years) | HR (95% CI) | P-value |
| TL (fusion mean) | | 23.2 (11.0-48.7) | <0.0001 | | 71.3 (20.0-253.7) | <0.0001 |
| ≤2.26 kb | 1.8 | | | 7.5 | | |
| >2.26 kb | not reached | | | not reached | | |
| IGHVstatus | | 4.6 (2.4-8.8) | <0.0001 | | 2.9 (1.0-8.1) | 0.04 |
| ≥98% | 2.9 | | | not reached | | |
| <98% | not reached | | | not reached | | |
| CD38 | | 3.0 (1.7-5.3) | 0.0003 | | 3.2 (1.1-9.1) | 0.03 |
| ≥20% | 3.0 | | | not reached | | |
| <20% | not reached | | | not reached | | |
| ZAP-70 | | 1.7 (1.0-2.9) | 0.07 | | 2.3 (0.9-6.2) | 0.08 |
| ≥20% | 6.0 | | | not reached | | |
| <20% | not reached | | | not reached | | |
| β2-M | | 3.1 (1.6-6.2) | 0.001 | | 3.1 (0.99-9.5) | 0.05 |
| ≥4 g/dL | 3.0 | | | 12.7 | | |
| <4 g/dL | Not reached | | | Not reached | | |
| Genetics | | 7.7 (3.1-18.9) | <0.0001 | | 10.1 (2.7-36.9) | 0.0004 |
| 11q−/17p− | 2.0 | | | 6.9 | | |
| N/O | not reached | | | not reached | | |

TL (fusion mean): The mean telomere length of the samples in which fusion events were detected IGHV status: <98% sequence homology with the closest germline sequence (mutated); ≥98% sequence homology with the closest germline sequence (unmutated)

β2-M: beta 2 microglobulin

11q− and 17p−: any FISH or karyotypic abnormality of 11q or 17p

N: No detectable cytogenetic aberration by FISH

O: Other cytogenetic abnormality (excluding 11q− or 17p−)

HR = Hazard ratio

95% CI = 95% confidence interval

TABLE 3

Clinical characteristics of the 184 CLL patient cohort.

| Factor | Subset | Number |
|---|---|---|
| Median Age | | 64 years |
| Range | | 27-95 years |
| Median Follow up | | 5.8 years |
| Required treatment | Treated | 75 |
| | Untreated | 104 |
| CD38 | <20% | 105 |
| | ≥20% | 53 |
| | Not Determined | 26 |
| Genetics | 11q⁻/17p⁻ | 21 |
| | N/O | 125 |
| | Not Determined | 38 |
| IGHV Status | <98% | 93 |
| | ≥98% | 45 |
| | Not Determined | 46 |
| ZAP-70 | <20% | 95 |
| | ≥20% | 59 |
| | Not Determined | 30 |
| β2-microglobulin | <4 mg/dL | 81 |
| | ≥4 mg/dL | 37 |
| | Not Determined | 56 |

TABLE 4

Analysis of concordant datasets combining telomere length with known prognostic markers.

| | | TTFT | | OS | |
|---|---|---|---|---|---|
| Parameter | n | HR (95% CI) | P-value | HR (95% CI) | P-value |
| TL + IGHV | | 141.2 (40.5-492.1) | <0.0001 | 72.4 (14.4-365.5) | <0.0001 |
| TL ≤ 2.26 kb + UM IGHV | 16 | | | | |
| TL > 2.26 kb + M IGHV | 79 | | | | |
| TL + CD38 | | 134.7 (35.5-512.1) | <0.0001 | 2915 (261.1-32550) | <0.0001 |
| TL ≤ 2.26 kb + CD38⁺ | 14 | | | | |
| TL > 2.26 kb + CD38⁻ | 88 | | | | |
| TL + ZAP-70 | | 29.3 (9.9-86.0) | <0.0001 | 681.2 (99.9-4645) | <0.0001 |
| TL ≤ 2.26 kb + ZAP-70⁺ | 16 | | | | |
| TL > 2.26 kb + ZAP-70⁻ | 80 | | | | |
| TL + cytogenetics | | 52.2 (14.8-186.3) | <0.0001 | 308.5 (44.1-2147) | <0.0001 |
| TL ≤ 2.26 kb + 11q⁻/17p⁻ | 13 | | | | |
| TL > 2.26 kb + Other | 105 | | | | |

*Analysis is shown for concordant cases only e.g. TL ≤ 2.26 kb/IGHV unmutated vs TL > 2.26 kb/IGHV mutated. Discordant datasets were not included in this analysis.
TL = telomere length
UM = IGHV unmutated cases: ≥98% sequence homology with the closest germline sequence
M = IGHV mutated cases: <98% sequence homology with the closest germline sequence

---

The invention claimed is:

1. A prognostic method for determining the progression of one or both of a cancerous disease and a precancerous condition characterized by telomere shortening comprising:
   i) by high-resolution telomere length analysis, determining a longest mean 7q telomere length at which telomere end-end fusion events can be detected in samples of cancerous or precancerous tissue from a control group of humans presenting with said cancerous disease or precancerous condition, this defining a threshold 7q telomere length providing the longest mean 7q telomere length at which telomeres become dysfunctional and capable of said telomere end-end fusion events;
   ii) identifying human control group samples having a mean telomere length that is less than said threshold telomere length;
   iii) calculating a human control group mean 7q telomere length from said control group samples to thereby provide a defined prognostic mean 7q telomere length for said cancerous disease or precancerous condition;
   iv) determining a mean human test 7q telomere length of a sample taken from a human patient suspected of having or presenting with said cancerous disease or precancerous condition; and
   v) comparing said mean test 7q telomere length to said defined prognostic mean 7q telomere length;

wherein a determination that said mean 7q test telomere length is less than said defined prognostic mean 7q telomere length is determinative that time to first treatment for cancer is poor and/or response to cancer treatment is poor and/or overall cancer survival is poor, and a determination that said mean 7q test telomere length is greater than said defined prognostic mean 7q telomere length is determinative that time to first treatment for cancer is good and/or response to cancer treatment is good and/or overall cancer survival is good;

further wherein said high-resolution telomere length analysis comprises a PCR reaction using primers specific for chromosome 7q and selected from the group consisting of:

GGGCACTGCCTCGCTTTGA; (SEQ ID NO: 41)

GCAGTGCTAAGACAGCAATGAgAAc; (SEQ ID NO: 42)

```
                                      (SEQ ID NO: 43)
CAGTGCTAAGACAGCAATGAg;

(SEQ ID NO: 44)
ATCGGCATTCCCCACACTGCCa;

(SEQ ID NO: 45)
ATATAAGATCGGCATTCCC;
and (SEQ ID NO: 46)
AGATCCACACCGTAGCGTg.
```

2. The method of claim 1 wherein step i) additionally comprises undertaking a PCR reaction using any one or more primers specific for chromosome XpYp selected from the group consisting of:

```
                                      (SEQ ID NO: 11)
TTGTCTCAGGGTCCTAGTG;

(SEQ ID NO: 12)
GGTTATCAACCAGGTGCTCT;

(SEQ ID NO: 13)
GGTTATCGACCAGGTGCTCC;

(SEQ ID NO: 14)
TGTGTCTGGAATTGGTGGGTT;

(SEQ ID NO: 15)
CCTAGTGTGTCTGGAATTGGTTC;

(SEQ ID NO: 1)
ACCAGGTTTTCCAGTGTGTT;

(SEQ ID NO: 16)
CAGGGACCGGGACAAATAGAC;

(SEQ ID NO: 4)
CCTGTAACGCTGTTAGGTAC;

(SEQ ID NO: 24)
ACCAGGGGCTGATGTAACG;

(SEQ ID NO: 25)
TCTCAGGGTCCTAGTGTG;

(SEQ ID NO: 26)
GTTGTCTCAGGGTCCTAG;

(SEQ ID NO: 27)
GGGGTTGTCTCAGGGTCC;

(SEQ ID NO: 28)
TTCTAGGGTTGTCTCAG;

(SEQ ID NO: 29)
TCTTCTAGGGTTGTCTC;

(SEQ ID NO: 30)
CTAATCTGCTCCCWCCCAC;

(SEQ ID NO: 31)
GTGAGAGCTCAAGGT GCAGAAG;

(SEQ ID NO: 32)
TGTCGGGGACTGGGTTAACAG;

(SEQ ID NO: 33)
GCTGAGAAAGACCTT TTCGTAC;
and (SEQ ID NO: 34)
CAAAGTGTTTGCATCAGTACCTCAC.
```

3. The method according to claim 1 wherein step i) additionally comprises undertaking a PCR reaction using primers specific for one or more of chromosome(s): 17p, 16p, 18q, 2p2, 11q and 12q, and selected from the group consisting of:

```
                                      (SEQ ID NO: 17)
GAATCCACGGATTGCTTTGTGTAC;

(SEQ ID NO: 2)
GGCTGAACTATAGCCTCTGC;

(SEQ ID NO: 5)
CCTGGCATGGTATTGACATG.

(SEQ ID NO: 18)
GTGAATAATCAAGGTCAGAGCA.

(SEQ ID NO: 19)
CCTGTGGGTCTAAAACCAGAAGG (SEQ ID NO: 20)
GAGCTGCGTTTTGCTGAGCAC.

(SEQ ID NO: 21)
CAGACCTTGGAGGCACGGCCTTCG.

(SEQ ID NO: 22)
GGGAGATCCACACCGTAGCA
and (SEQ ID NO: 23)
ACAGCCTTTTGGGGTACCGC.
```

4. The method according to claim 1 wherein said fusion event in part i) above is verified as being such by direct DNA sequence analysis.

5. The method according to claim 1 wherein, additionally said prognostic mean 7q telomere length of samples of tissue from a number of human individuals presenting with said cancerous disease or precancerous condition is determined by taking those samples that exhibit telomere fusion and averaging the mean telomere length of those samples.

6. The method according to claim 1 wherein said cancer is a hematological malignancy or a solid tumor.

7. The method according to claim 5 wherein said cancer is one of chronic lymphocytic leukemia (CLL), a myelodysplastic syndrome (MDS) or breast cancer.

8. The method according to claim 1 wherein said telomere length at which the telomere end-end fusion event can be detected is determined for a single chromosome.

\* \* \* \* \*

SEQUENCE LISTING

<160> NUMBER OF SEQ ID NOS: 46

<210> SEQ ID NO 1
<211> LENGTH: 20
<212> TYPE: DNA
<213> ORGANISM: Homo sapiens

<400> SEQUENCE: 1
accaggtttt ccagtgtgtt          20

<210> SEQ ID NO 2
<211> LENGTH: 20
<212> TYPE: DNA
<213> ORGANISM: Homo sapiens

<400> SEQUENCE: 2
ggctgaacta tagcctctgc          20

<210> SEQ ID NO 3
<211> LENGTH: 20
<212> TYPE: DNA
<213> ORGANISM: Homo sapiens

<400> SEQUENCE: 3
cttggtgtcg agagaggtag          20

-continued

```
<210> SEQ ID NO 4
<211> LENGTH: 20
<212> TYPE: DNA
<213> ORGANISM: Homo sapiens

<400> SEQUENCE: 4
cctgtaacgc tgttaggtac                                           20

<210> SEQ ID NO 5
<211> LENGTH: 20
<212> TYPE: DNA
<213> ORGANISM: Homo sapiens

<400> SEQUENCE: 5
cctggcatgg tattgacatg                                           20

<210> SEQ ID NO 6
<211> LENGTH: 20
<212> TYPE: DNA
<213> ORGANISM: Homo sapiens

<400> SEQUENCE: 6
tggtcttata cactgtgttc                                           20

<210> SEQ ID NO 7
<211> LENGTH: 25
<212> TYPE: DNA
<213> ORGANISM: Homo sapiens

<400> SEQUENCE: 7
agctagctat ctactctaac agagc                                     25

<210> SEQ ID NO 8
<211> LENGTH: 20
<212> TYPE: DNA
<213> ORGANISM: Homo sapiens

<400> SEQUENCE: 8
tctgaaagtg gaccaatcag                                           20

<210> SEQ ID NO 9
<211> LENGTH: 20
<212> TYPE: DNA
<213> ORGANISM: Homo sapiens

<400> SEQUENCE: 9
tctgaaagtg gacctatcag                                           20

<210> SEQ ID NO 10
<211> LENGTH: 21
<212> TYPE: DNA
<213> ORGANISM: Homo sapiens

<400> SEQUENCE: 10
agaatcctgt cctcaacaag t                                         21

<210> SEQ ID NO 11
<211> LENGTH: 19
<212> TYPE: DNA
<213> ORGANISM: Homo sapiens

<400> SEQUENCE: 11
ttgtctcagg gtcctagtg                                            19
```

<210> SEQ ID NO 12
<211> LENGTH: 20
<212> TYPE: DNA
<213> ORGANISM: Homo sapiens

<400> SEQUENCE: 12
ggttatcaac caggtgctct                                                   20

<210> SEQ ID NO 13
<211> LENGTH: 20
<212> TYPE: DNA
<213> ORGANISM: Homo sapiens

<400> SEQUENCE: 13
ggttatcgac caggtgctcc                                                   20

<210> SEQ ID NO 14
<211> LENGTH: 21
<212> TYPE: DNA
<213> ORGANISM: Homo sapiens

<400> SEQUENCE: 14
tgtgtctgga attggtgggt t                                                 21

<210> SEQ ID NO 15
<211> LENGTH: 23
<212> TYPE: DNA
<213> ORGANISM: Homo sapiens

<400> SEQUENCE: 15
cctagtgtgt ctggaattgg ttc                                               23

<210> SEQ ID NO 16
<211> LENGTH: 21
<212> TYPE: DNA
<213> ORGANISM: Homo sapiens

<400> SEQUENCE: 16
cagggaccgg gacaaataga c                                                 21

<210> SEQ ID NO 17
<211> LENGTH: 24
<212> TYPE: DNA
<213> ORGANISM: Homo sapiens

<400> SEQUENCE: 17
gaatccacgg attgctttgt gtac                                              24

<210> SEQ ID NO 18
<211> LENGTH: 22
<212> TYPE: DNA
<213> ORGANISM: Homo sapiens

<400> SEQUENCE: 18
gtgaataatc aaggtcagag ca                                                22

<210> SEQ ID NO 19
<211> LENGTH: 23
<212> TYPE: DNA
<213> ORGANISM: Homo sapiens

<400> SEQUENCE: 19

```
cctgtgggtc taaaaccaga agg                                              23

<210> SEQ ID NO 20
<211> LENGTH: 21
<212> TYPE: DNA
<213> ORGANISM: Homo sapiens

<400> SEQUENCE: 20
gagctgcgtt ttgctgagca c                                                21

<210> SEQ ID NO 21
<211> LENGTH: 24
<212> TYPE: DNA
<213> ORGANISM: Homo sapiens

<400> SEQUENCE: 21
cagaccttgg aggcacggcc ttcg                                             24

<210> SEQ ID NO 22
<211> LENGTH: 20
<212> TYPE: DNA
<213> ORGANISM: Homo sapiens

<400> SEQUENCE: 22
gggagatcca caccgtagca                                                  20

<210> SEQ ID NO 23
<211> LENGTH: 20
<212> TYPE: DNA
<213> ORGANISM: Homo sapiens

<400> SEQUENCE: 23
acagcctttt ggggtaccgc                                                  20

<210> SEQ ID NO 24
<211> LENGTH: 125
<212> TYPE: DNA
<213> ORGANISM: Homo sapiens

<400> SEQUENCE: 24
ggtccacttt cagagggtga aggtgagggt tagggttagg gttagggtta gggttagggt      60
tagggttagg gttagggtta gggttagggt tagggttagg gttagggtta gggttgggca     120
cactg                                                                 125

<210> SEQ ID NO 25
<211> LENGTH: 246
<212> TYPE: DNA
<213> ORGANISM: Homo sapiens

<400> SEQUENCE: 25
ggtccacttt cagagggtga aggtgagggt gagggtgagg gtgagggtga gggtgagggt      60
gagggtgagg gtgagggtga gggttagggt tagggttagg gttacggggt tagggttagg     120
gttagggtta gggttagggt agggttaggg ttagggttag ggttgggttg gggttgggt      180 tggggttggt tttcctgcta ctgccttagg tcccgacttg ccccacttag cttgtgggac     240
ctcctc                                                                246

<210> SEQ ID NO 26
<211> LENGTH: 18
<212> TYPE: DNA
<213> ORGANISM: Homo sapiens
```

<400> SEQUENCE: 26
gttgtctcag ggtcctag                                                    18

<210> SEQ ID NO 27
<211> LENGTH: 18
<212> TYPE: DNA
<213> ORGANISM: homo sapiens

<400> SEQUENCE: 27
ggggttgtct cagggtcc                                                    18

<210> SEQ ID NO 28
<211> LENGTH: 18
<212> TYPE: DNA
<213> ORGANISM: homo sapiens

<400> SEQUENCE: 28 ttctagggt tgtctcag                                                     18

<210> SEQ ID NO 29
<211> LENGTH: 18
<212> TYPE: DNA
<213> ORGANISM: homo sapiens

<400> SEQUENCE: 29
tcttctaggg gttgtctc                                                    18

<210> SEQ ID NO 30
<211> LENGTH: 19
<212> TYPE: DNA
<213> ORGANISM: homo sapiens

<400> SEQUENCE: 30
ctaatctgct cccwcccac                                                   19

<210> SEQ ID NO 31
<211> LENGTH: 22
<212> TYPE: DNA
<213> ORGANISM: homo sapiens

<400> SEQUENCE: 31
gtgagagctc aaggtgcaga ag                                               22

<210> SEQ ID NO 32
<211> LENGTH: 21
<212> TYPE: DNA
<213> ORGANISM: homo sapiens

<400> SEQUENCE: 32
tgtcggggac tgggttaaca g                                                21

<210> SEQ ID NO 33
<211> LENGTH: 22
<212> TYPE: DNA
<213> ORGANISM: homo sapiens

<400> SEQUENCE: 33
gctgagaaag accttttcgt ac                                               22

<210> SEQ ID NO 34
<211> LENGTH: 25
<212> TYPE: DNA

<213> ORGANISM: homo sapiens

<400> SEQUENCE: 34
caaagtgttt gcatcagtac ctcac                                    25

<210> SEQ ID NO 35
<211> LENGTH: 21
<212> TYPE: DNA
<213> ORGANISM: homo sapiens

<400> SEQUENCE: 35
cccacacagt catctattgt t                                        21

<210> SEQ ID NO 36
<211> LENGTH: 25
<212> TYPE: DNA
<213> ORGANISM: homo sapiens

<400> SEQUENCE: 36
gaggtgcagt agtgggatc taact                                     25

<210> SEQ ID NO 37
<211> LENGTH: 20
<212> TYPE: DNA
<213> ORGANISM: homo sapiens

<400> SEQUENCE: 37
gggacagcat attctggttt                                          20

<210> SEQ ID NO 38
<211> LENGTH: 21
<212> TYPE: DNA
<213> ORGANISM: homo sapiens

<400> SEQUENCE: 38
gcacagcctt ttggggtacc a                                        21

<210> SEQ ID NO 39
<211> LENGTH: 25
<212> TYPE: DNA
<213> ORGANISM: homo sapiens

<400> SEQUENCE: 39
agtgggagat ccacaccgta gcgtg                                    25

<210> SEQ ID NO 40
<211> LENGTH: 26
<212> TYPE: DNA
<213> ORGANISM: homo sapiens

<400> SEQUENCE: 40
ccatgcagtg ctaagacagc aatgag                                   26

<210> SEQ ID NO 41
<211> LENGTH: 19
<212> TYPE: DNA
<213> ORGANISM: homo sapiens

<400> SEQUENCE: 41
gggcactgcc tcgctttga                                           19

<210> SEQ ID NO 42
<211> LENGTH: 25

```
<212> TYPE: DNA
<213> ORGANISM: homo sapiens

<400> SEQUENCE: 42
gcagtgctaa gacagcaatg agaac                                          25

<210> SEQ ID NO 43
<211> LENGTH: 21
<212> TYPE: DNA
<213> ORGANISM: homo sapiens

<400> SEQUENCE: 43
cagtgctaag acagcaatga g                                              21

<210> SEQ ID NO 44
<211> LENGTH: 22
<212> TYPE: DNA
<213> ORGANISM: homo sapiens

<400> SEQUENCE: 44
atcggcattc cccacactgc ca                                             22

<210> SEQ ID NO 45
<211> LENGTH: 19
<212> TYPE: DNA
<213> ORGANISM: homo sapiens

<400> SEQUENCE: 45
atataagatc ggcattccc                                                 19

<210> SEQ ID NO 46
<211> LENGTH: 19
<212> TYPE: DNA
<213> ORGANISM: homo sapiens

<400> SEQUENCE: 46
agatccacac cgtagcgtg                                                 19
```